United States Patent
Tsuji et al.

(10) Patent No.: US 7,488,491 B2
(45) Date of Patent: Feb. 10, 2009

(54) USE OF GLYCOSYLCERAMIDES AS ADJUVANTS FOR VACCINES AGAINST INFECTIONS AND CANCER

(75) Inventors: Moriya Tsuji, New York, NY (US); Gloria Gonzalez-Aseguinolaza, Baranain (ES); Yasuhiko Koezuka, Gunma (JP)

(73) Assignee: New York University, New York, NY (US)

( * ) Notice: Subject to any disclaimer, the term of this patent is extended or adjusted under 35 U.S.C. 154(b) by 0 days.

(21) Appl. No.: 10/206,155

(22) Filed: Jul. 25, 2002

(65) Prior Publication Data

US 2003/0157135 A1    Aug. 21, 2003

Related U.S. Application Data

(60) Provisional application No. 60/308,056, filed on Jul. 25, 2001.

(51) Int. Cl.
    *A61K 47/00*    (2006.01)
(52) U.S. Cl. .......................... 424/278.1; 435/6; 514/25
(58) Field of Classification Search ................ 514/772, 514/23, 24–26, 895; 435/5, 235.1; 424/1.11, 424/1.65, 60.1, 184.1, 204.1, 278.1, 281.1
    See application file for complete search history.

(56) References Cited

U.S. PATENT DOCUMENTS 6,555,375 B1    4/2003    Golovko

FOREIGN PATENT DOCUMENTS

EP    1 018 548 A1    7/2000
WO    WO-99/15627 A1    4/1999

OTHER PUBLICATIONS

Gonzalez-Aseguinolaza et al. alpha-Galactosylceramide-activated Valpha14 natural killer T cells mediate protection against murine malaria. PNAS, Jul. 18, 2000, vol. 97, No. 15, pp. 8461-8466.*
Orange et al. Viral evasion of natural killer cells. Review: Nature Immunology, Vo. 3, No. 11, 2002, pp. 1006-1012.*
Tsuji et al. Recombinant Sindbis viruses expressing a cytotoxic T-lymphocyte epitope of a malaria parasite or of influenza virus elicit protection against the corresponding pathogen in mice. Journal of Virology, 1998, vol. 72, No. 8, pp. 6907-6910.*
Giaccone et al. A phase I study of the Natural Killer T-cell ligand alpha-galactosylceramide (KRN7000) in patients with solid tumors. Clinical Cancer Research, 2002, vol. 8, pp. 3702-3709.*
Tsuji et al. Recombinant Sindbis viruses expressing a cytotoxic T-Lymphoctye epitope of a malaria parasite or of influenza virus elicit protection against the corresponding pathogen in mice. Journal of Virology, Aug. 1998, V. 72, No. 8, p. 6907-6910.*
Rodrigues et al. Single immunization dose of recombinant adenovirus efficiently induces CD8+ T cell-mediated protective immunity against malaria. The Journal of Immunology, 1997, vol. 158, p. 1268-1274.*

Gonzalez-Aseguinolaza et al. alpha-galactosylceramide-activated Valpha14 natural killer T cells mediate protection against murine malaria. PNAS, Jul. 18, 2000; vol. 97, No. 15, p. 8461-8466.*
S. Ishihara et al., "Alpha-Glycosylceramides Enhance the Antitumor Cytotoxicity of Hepatic Lymphocytes Obtained from Cancer Patients by Activating CD3-CD56+ NK Cells In Vitro," *The Journal of Immunology*, 2000, vol. 165, pp. 1659-1664.
Gonzalez-Aseguinolaza et al., "Natural Killer T Cell Ligand α-Galactosylceramide Enhances Protective Immunity Induced by Malaria Vaccines", J. Exp. Med., 2002, 195:617-624.
Hidemitsu Kitamura et al., "The Natural Killer T (NKT) Cell Ligand α-Galactosylceramide Demonstrates Its Immunopotentiating Effect by Inducing Interleukin (IL)-12 Production by Dendritic Cells and IL-12 Receptor Expression on NKT Cells," *J. Exp. Med.* 189(7):1121-1127 (Apr. 5, 1999).
Olivier Adotevi, at al., "B Subunit of Shiga Toxin-Based Vaccines Synergize with α-Galactosylceramide to Break Tolerance against Self Antigen and Elicit Antiviral Immunity[1]," *The Journal of Immunology*, 2007, 179, p. 3371-3379.
Takeshi Kinjo, et al., "NKT cells play a limited role in the neutrophilic inflammatory responses and host defense to pulmonary infection with *Pseudomonas aeruginosa*," *Microbes and Infection* 2006, 8, p. 2679-2685.
Dan H. Barouch, et al., "Augmentation and Suppression of Immune Responses to an HIV-1 DNA Vaccine by Plasmid Cytokine/Ig Administration," *The Journal of Immunology*, 1998, 161, p. 1875-1882.
Hsin-Wei Chen, et al., "Suppression of Immune Response and Protective Immunity to a Japanese Encephatilis Virus DNA Vaccine by Coadministration of an IL-12-Expressing Plasmid," *The Journal of Immunology*, 2001, 166, p. 7419-7426.
Cristina T. Fonseca, et al., "Co-administration of plasmid expressing IL-12 with 14-kDa *Schistosoma mansoni* fatty acid-binding protein cDNA alters immunie response profiles and fails to enhance protection induced by Sm14 DNA vaccine alone," *Microbes and Infection* 2006, 8, p. 2509-2516.
Phillip Scott, et al., "IL-12 as an adjuvant for cell-mediated immunity," *Seminars in Immunology*, 1997, 9, p. 285-291.
Luis C. C. Afonso, et al., "The Adjuvant Effect of Interleukin-12 in a Vaccine Against Leishmania major," *Science*, 1994, 263, p. 235-237.
Yen-Hung Chow, et al., "Improvement of Hepatitis B Virus DNA Vaccines by Plasmids Coepressing Hepatitis B Surface Antigen and Interleukin-2," *Journal of Virology*, 1997, 71, p. 169-178.
Jan. 2008 Manuscript entitled "Enhancement of HIV DNA vaccine immunogenicity by the NK T Cell Ligand, alpha-galactosylceramide".

* cited by examiner

*Primary Examiner*—Emily M. Le
(74) *Attorney, Agent, or Firm*—Darby & Darby P.C.

(57) ABSTRACT

The present invention relates to methods and compositions for augmenting an immunogenicity of an antigen in a mammal, comprising administering said antigen together with an adjuvant composition that includes glycosylceramide, preferably α-galactosylceramide (α-GalCer). According to the present invention, the use of glycosylceramide as an adjuvant is attributed at least in part to the enhancement and/or extension of antigen-specific Th1-type responses, in particular, CD8+ T cell responses. The methods and compositions of the present invention can be useful for prophylaxis and treatment of various infectious and neoplastic diseases.

17 Claims, 12 Drawing Sheets

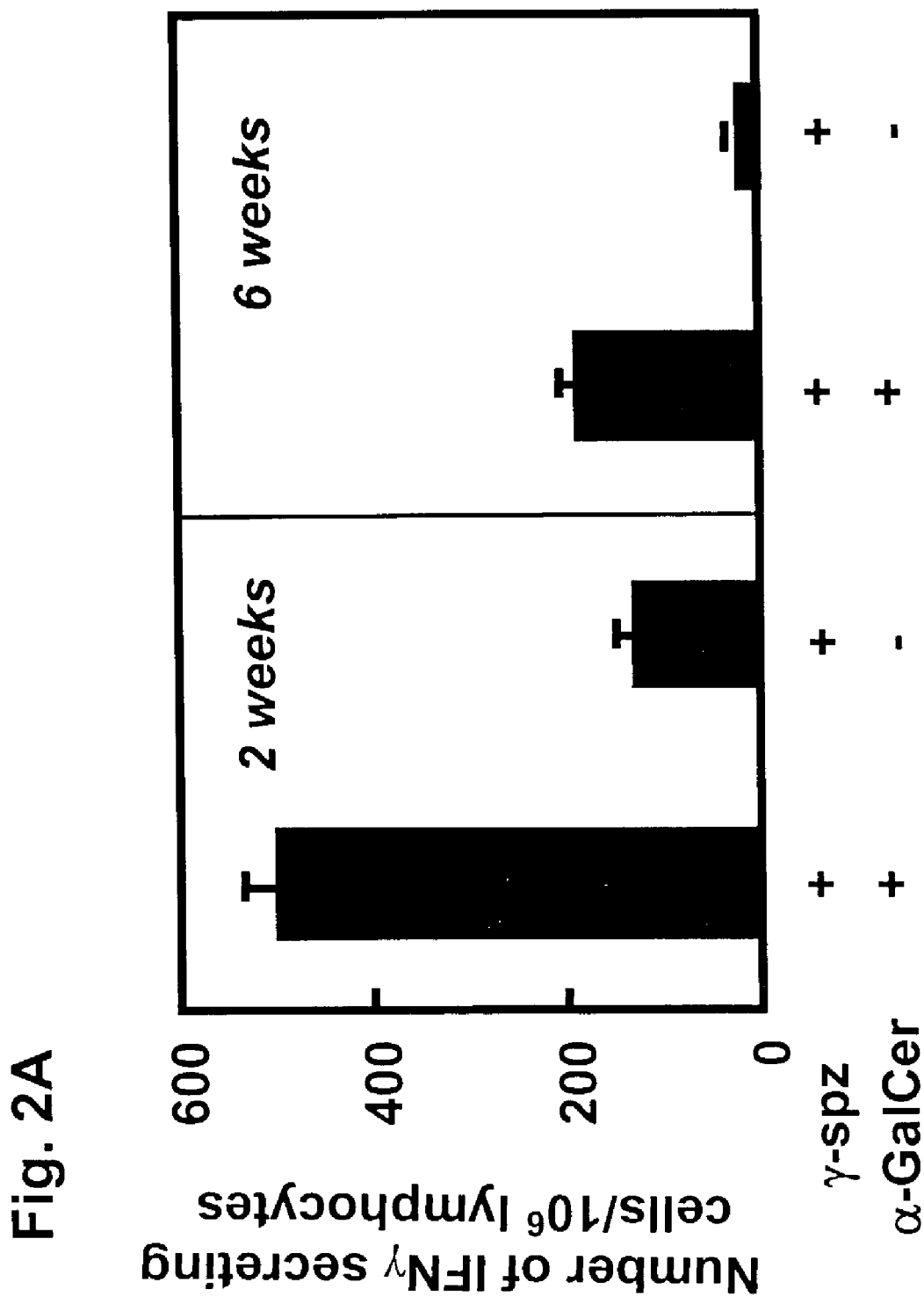

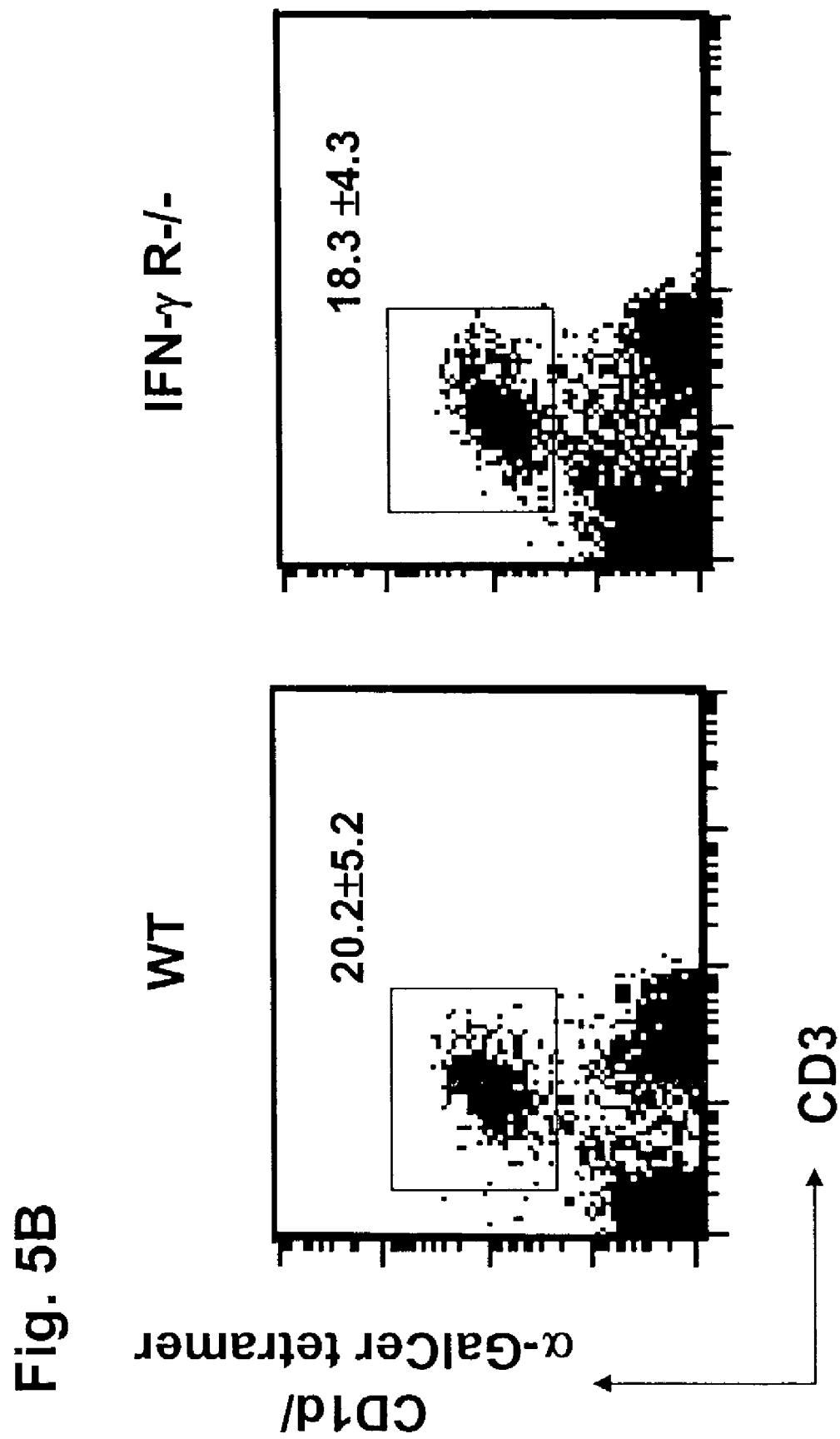

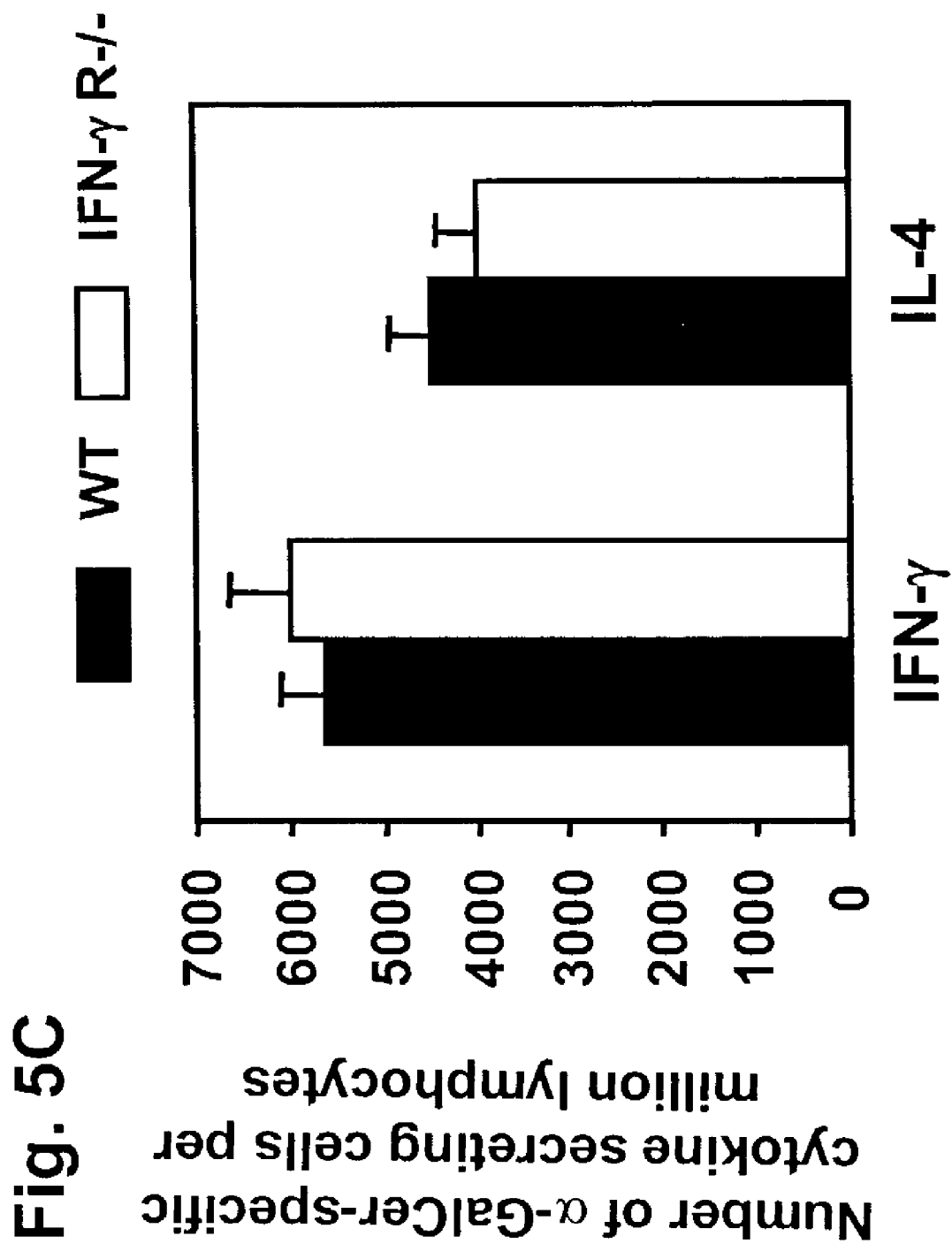

SEQUENCE LISTING

<160> NUMBER OF SEQ ID NOS: 19

<210> SEQ ID NO 1

```
<211> LENGTH: 21
<212> TYPE: PRT
<213> ORGANISM: P. yoelii

<400> SEQUENCE: 1

Tyr Asn Arg Asn Ile Val Asn Arg Leu Leu Gly Asp Ala Leu Asn Gly
1               5                   10                  15

Lys Pro Glu Glu Lys
            20

<210> SEQ ID NO 2
<211> LENGTH: 9
<212> TYPE: PRT
<213> ORGANISM: P. yoelii

<400> SEQUENCE: 2

Ser Tyr Val Pro Ser Ala Glu Gln Ile
1               5

<210> SEQ ID NO 3
<211> LENGTH: 8
<212> TYPE: PRT
<213> ORGANISM: P. falciparum

<400> SEQUENCE: 3

Asn Val Asp Pro Asn Ala Asn Pro
1               5

<210> SEQ ID NO 4
<211> LENGTH: 20
<212> TYPE: PRT
<213> ORGANISM: P. falciparum

<400> SEQUENCE: 4

Glu Tyr Leu Asn Lys Ile Gln Asn Ser Leu Ser Thr Glu Trp Ser Pro
1               5                   10                  15

Cys Ser Val Thr
            20

<210> SEQ ID NO 5
<211> LENGTH: 10
<212> TYPE: PRT
<213> ORGANISM: HIV-1

<400> SEQUENCE: 5

Arg Gly Pro Gly Arg Ala Phe Val Thr Ile
1               5                   10

<210> SEQ ID NO 6
<211> LENGTH: 11
<212> TYPE: PRT
<213> ORGANISM: HIV-1

<400> SEQUENCE: 6

Lys Ala Phe Ser Pro Glu Val Ile Pro Met Phe
1               5                   10

<210> SEQ ID NO 7
<211> LENGTH: 8
<212> TYPE: PRT
<213> ORGANISM: HIV-1
```

```
<400> SEQUENCE: 7

Lys Ala Phe Ser Pro Glu Val Ile
 1               5

<210> SEQ ID NO 8
<211> LENGTH: 9
<212> TYPE: PRT
<213> ORGANISM: HIV-1

<400> SEQUENCE: 8

Thr Pro Gln Asp Leu Asn Met Met Leu
 1               5

<210> SEQ ID NO 9
<211> LENGTH: 9
<212> TYPE: PRT
<213> ORGANISM: HIV-1

<400> SEQUENCE: 9

Thr Pro Gln Asp Leu Asn Thr Met Leu
 1               5

<210> SEQ ID NO 10
<211> LENGTH: 10
<212> TYPE: PRT
<213> ORGANISM: HIV-1

<400> SEQUENCE: 10

Asp Thr Ile Asn Glu Glu Ala Ala Glu Trp
 1               5                  10

<210> SEQ ID NO 11
<211> LENGTH: 10
<212> TYPE: PRT
<213> ORGANISM: HIV-1

<400> SEQUENCE: 11

Lys Arg Trp Ile Ile Leu Gly Leu Asn Lys
 1               5                  10

<210> SEQ ID NO 12
<211> LENGTH: 9
<212> TYPE: PRT
<213> ORGANISM: HIV-1

<400> SEQUENCE: 12

Gln Ala Thr Gln Glu Val Lys Asn Trp
 1               5

<210> SEQ ID NO 13
<211> LENGTH: 9
<212> TYPE: PRT
<213> ORGANISM: HIV-1

<400> SEQUENCE: 13

Arg Leu Arg Pro Gly Gly Lys Lys Lys
 1               5

<210> SEQ ID NO 14
<211> LENGTH: 9
<212> TYPE: PRT
<213> ORGANISM: HIV-1
```

```
<400> SEQUENCE: 14

Ser Leu Tyr Asn Thr Val Ala Thr Leu
1               5

<210> SEQ ID NO 15
<211> LENGTH: 12
<212> TYPE: PRT
<213> ORGANISM: P. falciparum

<400> SEQUENCE: 15

Asn Ala Asn Pro Asn Ala Asn Pro Asn Ala Asn Pro
1               5                   10

<210> SEQ ID NO 16
<211> LENGTH: 9
<212> TYPE: PRT
<213> ORGANISM: influenza A virus

<400> SEQUENCE: 16

Thr Tyr Gln Arg Thr Arg Ala Leu Val
1               5

<210> SEQ ID NO 17
<211> LENGTH: 25
<212> TYPE: DNA
<213> ORGANISM: Artificial Sequence
<220> FEATURE:
<223> OTHER INFORMATION: forward primer for RT-PCR

<400> SEQUENCE: 17
ggggattggt tttgacgttt ttgcg                                   25

<210> SEQ ID NO 18
<211> LENGTH: 30
<212> TYPE: DNA
<213> ORGANISM: Artificial Sequence
<220> FEATURE:
<223> OTHER INFORMATION: reverse primer for RT-PCR

<400> SEQUENCE: 18
aagcattaaa taaagcgaat acatccttat                              30

<210> SEQ ID NO 19
<211> LENGTH: 24
<212> TYPE: DNA
<213> ORGANISM: Artificial Sequence
<220> FEATURE:
<223> OTHER INFORMATION: fluorogenic probe, PyNYU

<400> SEQUENCE: 19
caattggttt accttttgct cttt                                    24
```

USE OF GLYCOSYLCERAMIDES AS ADJUVANTS FOR VACCINES AGAINST INFECTIONS AND CANCER

Figure 1A:
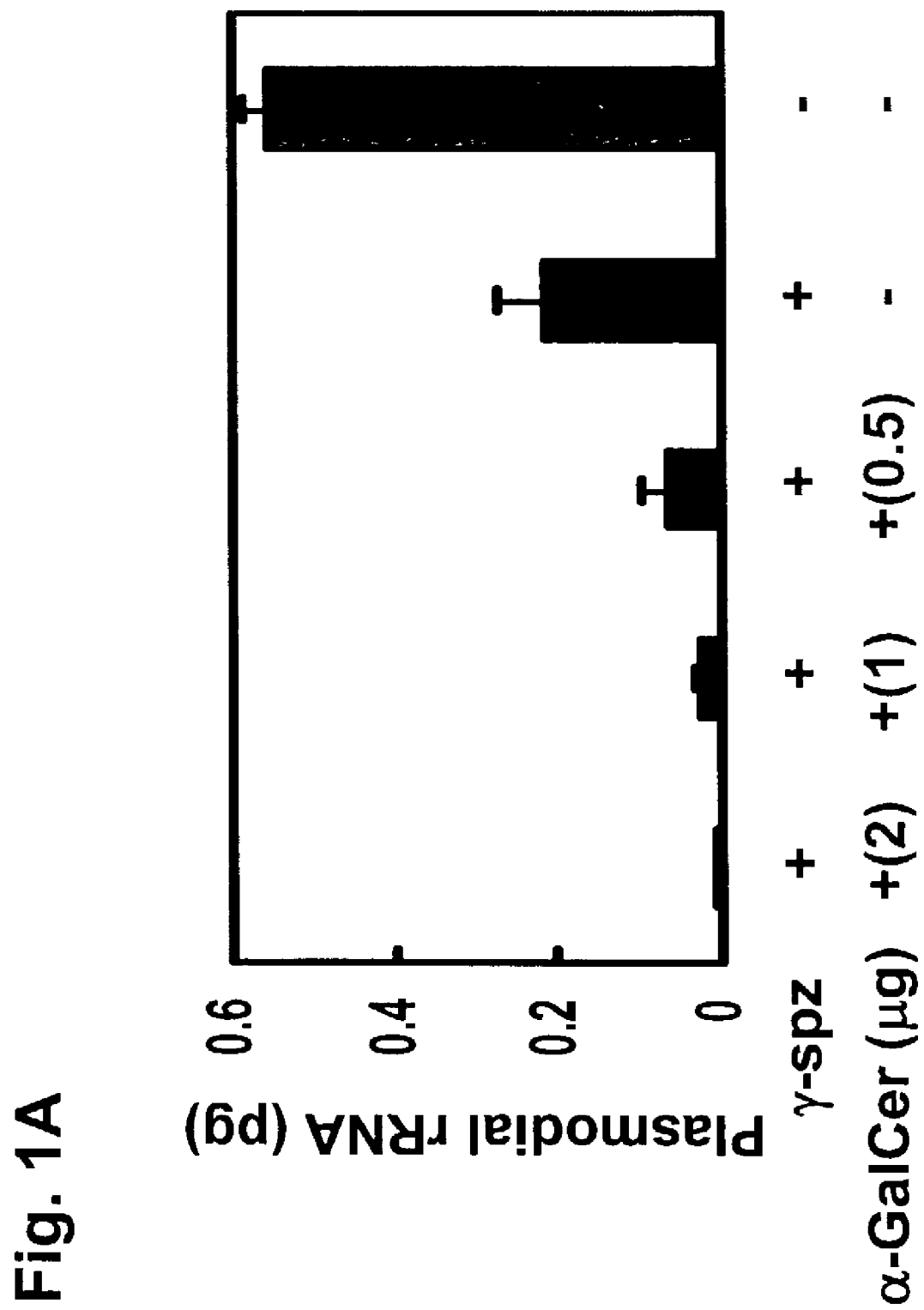

This application claims priority under 35 U.S.C. §119(e) from U.S. Provisional Patent Application Ser. No. 60/308,056 filed Jul. 25, 2001, which is incorporated herein by reference in its entirety.

The research leading to the present invention was supported, in part, by the grants AI-01682, AI-40656, and AI-47840 from the National Institutes of Health. Accordingly, the U.S. government has certain rights in the invention.

FIELD OF THE INVENTION

The present invention relates to the use of glycosylceramides as adjuvants to augment the immunogenicity of various infectious and tumor antigens.

BACKGROUND OF THE INVENTION

The successful elimination of pathogens, neoplastic cells, or self-reactive immune mechanisms following prophylactic or therapeutic immunization depends to a large extent on the ability of the host's immune system to become activated in response to the immunization and mount an effective response, preferably with minimal injury to healthy tissue.

The rational design of vaccines initially involves identification of immunological correlates of protection—the immune effector mechanism(s) responsible for protection against disease—and the subsequent selection of an antigen that is able to elicit the desired adaptive response. Once this appropriate antigen has been identified, it is essential to deliver it effectively to the host's immune system.

In the design of effective vaccines, immunological adjuvants serve as critical components, which accelerate, prolong, and/or enhance an antigen-specific immune response as well as provide the selective induction of the appropriate type of response.

New vaccines are presently under development and in testing for the control of various neoplastic, autoimmune and infectious diseases, including human immunodeficiency virus (HIV) and tuberculosis. In contrast to older vaccines which were typically based on live-attenuated or non-replicating inactivated pathogens, modem vaccines are composed of synthetic, recombinant, or highly purified subunit antigens. Subunit vaccines are designed to include only the antigens required for protective immunization and are believed to be safer than whole-inactivated or live-attenuated vaccines. However, the purity of the subunit antigens and the absence of the self-adjuvanting immunomodulatory components associated with attenuated or killed vaccines often result in weaker immunogenicity.

The immunogenicity of a relatively weak antigen can be enhanced by the simultaneous or more generally conjoined administration of the antigen with an "adjuvant", usually a substance that is not immunogenic when administered alone, but will evoke, increase and/or prolong an immune response to an antigen. In the absence of adjuvant, reduced or no immune response may occur, or worse the host may become tolerized to the antigen.

Adjuvants can be found in a group of structurally heterogeneous compounds (Gupta et al., 1993, Vaccine, 11:293-306). Classically recognized examples of adjuvants include oil emulsions (e.g., Freund's adjuvant), saponins, aluminium or calcium salts (e.g., alum), non-ionic block polymer surfactants, lipopolysaccharides (LPS), mycobacteria, tetanus toxoid, and many others. Theoretically, each molecule or substance that is able to favor or amplify a particular situation in the cascade of immunological events, ultimately leading to a more pronounced immunological response can be defined as an adjuvant.

In principle, through the use of adjuvants in vaccine formulations, one can (1) direct and optimize immune responses that are appropriate or desirable for the vaccine; (2) enable mucosal delivery of vaccines, i.e., administration that results in contact of the vaccine with a mucosal surface such as buccal or gastric or lung epithelium and the associated lymphoid tissue; (3) promote cell-mediated immune responses; (4) enhance the immunogenicity of weaker immunogens, such as highly purified or recombinant antigens; (5) reduce the amount of antigen or the frequency of immunization required to provide protective immunity; and (6) improve the efficacy of vaccines in individuals with reduced or weakened immune responses, such as newborns, the aged, and immunocompromised vaccine recipients.

Although little is known about their mode of action, it is currently believed that adjuvants augment immune responses by one of the following mechanisms: (1) increasing the biological or immunologic half-life of antigens (see, e.g., Lascelles, 1989, Vet. Immunol. Immunopathol., 22: 15-27; Freund, 1956, Adv. Tuber. Res., 7: 130-147); (2) improving antigen delivery to antigen-presenting cells (APCs), as well as antigen processing and presentation by the APCs (see, e.g., Fazekas de St. Groth et al., Immunol. Today, 19: 448-454, 1998), e.g., by enabling antigen to cross endosomal membranes into the cytosol after ingestion of antigen-adjuvant complexes by APCs (Kovacsovics-Bankowski et al., Science, 1995, 267: 243-246); (3) mimicking microbial structures leading to improved recognition of microbially-derived antigens by the pathogen-recognition receptors (PRRs), which are localized on accessory cells from the innate immune system (Janeway, 1989, Cold Spring Harbor Symp. Quant. Biol., 54:1-13; Medzhitov, 1997, Cell, 91:295-298; Rook, 1993, Immunol. Today, 14:95-96); (4) mimicking danger-inducing signals from stressed or damaged cells which serve to initiate an immune response (see, e.g., Matzinger, 1994, Annu. Rev. Immunol., 12:991-209), (5) inducing the production of immunomodulatory cytokines (see, e.g., Nohria, 1994, Biotherapy, 7:261-269; Iwasaki et al., 1997, J. Immunol., 158:4591-4601; Maecker et al., 1997, Vaccine, 15:1687-1696); (6) biasing the immune response towards a specific subset of the immune system (e.g., generating Th1- or Th2-polarized response [see below], etc.) (Janssen et al., Blood, 97:2758-2763, 2001; Yamamoto et al., Scand. J. Immunol., 53:211-217, 2001; Weiner G. J., J. Leukoc. Biol., 68:455-63, 2000; Lucey, Infect. Dis. Clin. North Am., 13:1-9, 1999), and (7) blocking rapid dispersal of the antigen challenge (the "depot effect") (Hood et al., *Immunology*, Second Ed., 1984, Benjamin/Cummings: Menlo Park, Calif.; St Clair et al., Proc. Natl. Acad. Sci. U.S.A., 96:9469-9474, 1999; Ahao et al., J. Pharm. Sci., 85:1261-1270, 1996; Morein et al., Vet. Immunol. Immunopathol., 54:373-384, 1996). (See also reviews by Schijns, Curr. Opin. Immunol., 12: 456-463, 2000; Vogel, Clin. Infect. Dis., 30 [Suppl. 3]: S266-70, 2000; Singh and O'Hagan, Nature Biotechnol., 17: 1075-81, 1999; Cox and Coulter, Vaccine, 15: 248-256, 1997).

Recent observations strongly suggest that endogenously produced cytokines act as essential communication signals elicited by traditional adjuvants. The redundancy of the cytokine network makes it difficult to ascribe the activity of a particular adjuvant to one or more cytokines. Cytokines crucial for immunogenicity may include the proinflammatory (Type 1) substances: interferon (IFN)-$\alpha/\beta$, tumor necrosis factor (TNF)-α, interleukin (IL)-1, IL-6, IL-12, IL-15 and IL-18, which influence antigen presentation. Others may act more downstream during clonal expansion and differentiation of T and B cells, with IL-2, IL-4 and IFN-γ as prototypes (Brewer et al., 1996, Eur. J. Immunol., 26:2062-2066; Smith et al., 1998, Immunology, 93:556-562). Adjuvants that enhance immune responses through the induction of IFN-γ and delayed-type hypersensitivity also elicit the production of IgG subclasses that are the most active in complement-mediated lysis and in antibody-dependent cell-mediated-cytotoxicity effector mechanisms (e.g., IgG2a in mice and IgG1 in humans) (Allison, Dev. Biol. Stand., 1998, 92:3-11; Unkeless, Annu. Rev. Immunol., 1988, 6:251-81; Phillips et al., Vaccine, 1992, 10:151-8).

Clearly, some adjuvants may perform more than one function. For example, purified microbial components such as LPS or extracts of Toxoplasma gondii rapidly increase not only the number of antigen-presenting dendritic cells (DC) and their migration but also IL-12 production (Souza et al., 1997, J. Exp. Med., 186:1819-1829).

As different adjuvants may have diverse mechanisms of action, their being chosen for use with a particular vaccine may be based on the route of administration to be employed, the type of immune responses desired (e.g., antibody-mediated, cell-mediated, mucosal, etc.), and the particular inadequacy of the primary antigen.

The benefit of incorporating adjuvants into vaccine formulations to enhance immunogenicity must be weighed against the risk that these agents will induce adverse local and/or systemic reactions. Local adverse reactions include local inflammation at the injection site and, rarely, the induction of granuloma or sterile abscess formation. Systemic reactions to adjuvants observed in laboratory animals include malaise, fever, adjuvant arthritis, and anterior uveitis (Allison et al., Mol. Immunol., 1991, 28:279-84; Waters et al., Infect. Immun., 1986, 51:816-25). Such reactions often are caused by the interaction of the adjuvant and the antigen itself, or may be due to the type of response to a particular antigen the adjuvant produces, or the cytokine profile the adjuvant induces.

Thus, many potent immunoadjuvants, such as Freund's Complete or Freund's Incomplete Adjuvant, are toxic and are therefore useful only for animal research purposes, not human vaccinations. Currently, aluminum salts and MF59 are the only vaccine adjuvants approved for human use. Of the novel adjuvants under evaluation, immunostimulatory molecules such as the lipopolysaccharide-derived MPL and the saponin derivative QS-21 appear most promising, although doubts have been raised as to their safety for human use. Preclinical work with particulate adjuvants, such as the MF59 microemulsion and lipid-particle immuno-stimulating complexes (ISCOMs), suggest that these molecules are also themselves potent elicitors of humoral and cellular immune responses. In addition, preclinical data on CpG oligonucleotides appear to be encouraging, particularly with respect to their ability to manipulate immune responses selectively. While all these adjuvants show promise, the development of more potent novel adjuvants may allow novel vaccines to be developed and both novel and existing vaccines to be used as therapeutic as well as improved prophylactic agents.

Recently, a novel lymphoid lineage, natural killer T (NKT) cells, distinct from mainstream T cells, B cells and NK cells, has been identified (Arase et al., 1992, Proc. Natl Acad. Sci. USA, 89:6506; Bendelac et al., 1997, Annu. Rev. Immunol., 15:535). These cells are characterized by co-expression of NK cell receptors and semi-invariant T cell receptors (TCR) encoded by Vα14 and Jα281 gene segments in mice and Vα24 and JαQ gene segments in humans. The activation of NKT cells in vivo promptly induces a series of cellular activation events leading to the activation of innate cells such as natural killer (NK) cells and dendritic cells (DC), the activation of adaptive cells such as B cells and T cells, the induction of co-stimulatory molecules and the abrupt release of cytokines such as interleukin-4 (IL-4) and interferon-γ (IFN-γ) (Burdin et al., Eur. J. Immunol. 29: 2014-2025, 1999; Carnaud et al., J. Immunol., 163: 4647-4650, 1999; Kitamura et al., J. Exp. Med., 189: 1121-1128, 1999; Kitamura et al., Cell Immunol., 199: 37-42, 2000; Aderem and Ulevitch, Nature, 406: 782-787, 2000). In addition, activated NKT cells can themselves bring about killing mediated by Fas and perforin. The full activation cascade can be recruited by the engagement of NKT TCR. Alternatively, powerful T-helper-cell type 1 (Th1) functions can be selectively triggered by cytokines such as interleukin-12 (IL-12) released by infected macrophages or DC. These functions are believed likely to be correlated with the important role of NKT cells in conditions such as autoimmune diabetes, rejection of established tumours or the prevention of chemically induced tumours (Yoshimoto et al, 1995, Science, 270: 1845; Hammond et al., J. Exp. Med., 187: 1047-1056, 1998; Kawano et al., 1998, Proc. Natl. Acad. Sci. USA, 95: 5690; Lehuen et al., J. Exp. Med., 188: 1831-1839, 1998; Wilson et al., Nature, 391: 177-181, 1998; Smyth et al., J. Exp. Med., 191: 661-668, 2000). Finally, NKT cells are thought to contribute to antimicrobial immunity through their capacity to influence the Th1-Th2 polarization (Cui et al., J. Exp. Med., 190: 783-792, 1999; Singh et al., J. Immunol., 163: 2373-2377, 1999; Shinkai and Locksley, J. Exp. Med., 191: 907-914, 2000). These cells are therefore implicated as key effector cells in innate immune responses. However, the potential role of NKT cells in the development of adaptive immune responses remains unclear.

Recently, it was demonstrated that NKT cells can be activated both in vitro and in vivo by α-galactosyl-ceramide (α-GalCer), a glycolipid originally extracted from Okinawan marine sponges (Natori et al., Tetrahedron, 50: 2771-2784, 1994), or its synthetic analog KRN 7000 [(2S,3S,4R)-1—O-(α-D-galactopyranosyl)-2-(N-hexacosanoylamino)-1,3,4,-octadecanetriol] which can be obtained from Pharmaceutical Research Laboratories, Kirin Brewery (Gumna, Japan) or synthesized as described previously (see, e.g., Kobayashi et al., 1995, Oncol. Res., 7:529-534; Kawano et al., 1997, Science, 278:1626-9; Burdin et al., 1998, J. Immunol., 161: 3271; Kitamura et al., 1999, J. Exp. Med., 189:1121; U.S. Pat. No. 5,936,076). Thus, it was shown that α-GalCer can stimulate NK activity and cytokine production by NKT cells and exhibits potent antitumor activity in vivo (Kawano et al., 1997, supra; Kawano et al., 1998, Proc. Natl Acad. Sci. USA, 95:5690; Kitamura et al., 1999, supra). Kitamura et al. (1999, supra) demonstrated that the immunostimulating effect of α-GalCer was initiated by CD40-CD40L-mediated NKT-DC interactions. As the immunoregulatory functions of α-GalCer were absent in both CD1d$^{-/-}$ and NKT-deficient mice, this indicates that α-GalCer has to be presented by the MHC class I-like molecule CD1d.

CD1 is a conserved family of non-polymorphic genes related to MHC that seems to have evolved to present lipid and glycolipid antigens to T cells and in this way participates in both an innate and an adaptive pathway of antigen recognition (reviewed by Park and Bendelac, Nature, 406: 788-792, 2000; see also Calabi et al., Eur. J. Immunol., 19: 285-292, 1989; Porcelli and Modlin, Annu. Rev. Immunol., 17: 297-329, 1999). It comprises up to five distinct genes (isotypes) that can be separated into two groups on the basis of sequence homology. Group 1, which comprises CD1a, CD1b, CD1c and CD1e, is present in humans but absent from mouse and rat. Group2, which includes CD1d, is found in all species studied so far, including humans.

CD1 isotypes are expressed selectively by antigen-presenting cells such as dendritic cells (DCs), macrophages and subsets of B cells, but apart from CD1d expression in hepatocytes they are generally not expressed in solid tissues (Porcelli et al., supra; Bendelac et al., Annu. Rev. Immunol., 15: 535-562, 1997).

α-GalCer is recognized in picomolar concentrations by those among mouse and human CD1d-restricted lymphocytes that express a semi-invariant TCR and exert potent effector and regulatory functions (Kawano et al., Science, 278: 1626-1629, 1997). CD1d/α-GalCer complex is, in turn, recognized by the antigen receptors of mouse Vα14 and human Vα24 natural killer T (NKT) cells (Bendelac et al., Science, 268: 863-865, 1995; Bendelac et al., Annu. Rev. Immunol., 15: 535-562, 1997; Park et al., Eur. J. Immunol., 30: 620-625, 2000).

Upon binding to CD1d, α-GalCer was demonstrated to activate murine NKT cells both in vivo and in vitro (Kawano et al., 1997, Science, 278:1626-1629; Burdin et al., 1998, J. Immunol., 161:3271-3281), and human NKT cells in vitro (Spada et al., 1998, J. Exp. Med., 188:1529-1534; Brossay et al., 1998, J. Exp. Med. 188:1521-1528). For example, α-GalCer was shown to display NKT-mediated anti-tumor activity in vitro by activating human NKT cells (Kawano et al., 1999, Cancer Res., 59:5102-5105).

In addition to α-GalCer, other glycosylceramides having α-anomeric conformation of sugar moiety and 3,4-hydroxyl groups of the phytosphingosine (such as α-glucosylceramide [α-GlcCer], Galα1-6Galα1-1'Cer, Galα1-6Glcα1-1'Cer, Galα1-2Galα1-1'Cer, and Galβ1-3Galα1-1'Cer) have been demonstrated to stimulate proliferation of Vα14 NKT cells in mice, although with lower efficiency (Kawano et al., Science, 278: 1626-1629, 1997). By testing a panel of α-GalCer analogs for reactivity with mouse Vα14 NKT cell hybridomas, Brossay et al. (J. Immunol., 161: 5124-5128, 1998) determined that nearly complete truncation of the α-GalCer acyl chain from 24 to 2 carbons does not significantly affect the mouse NKT cell response to glycolipid presented by either mouse CD1 or its human homolog.

It has been also demonstrated that in vivo administration α-GalCer not only causes the activation of NKT cells to induce a strong NK activity and cytokine production (e.g., IL-4, IL-12 and IFN-γ) by CD1d-restricted mechanisms, but also induces the activation of immunoregulatory cells involved in acquired immunity (Nishimura et al., 2000, Int. Immunol., 12: 987-994). Specifically, in addition to the activation of macrophages and NKT cells, it was shown that in vivo administration of α-GalCer resulted in the induction of the early activation marker CD69 on CD4+ T cells, CD8+ T cells, and B cells (Burdin et al., 1999, Eur. J. Immunol. 29: 2014; Singh et al., 1999, J. Immunol. 163: 2373; Kitamura et al., 2000, Cell. Immunol. 199:37; Schofield et al., 1999, Science 283: 225; Eberl et al., 2000, J. Immunol., 165:4305-4311). These studies open the possibility that α-GalCer may play an equally important role in bridging not only innate immunity mediated by NKT cells, but also adaptive immunity mediated by B cells, T helper (Th) cells and T cytotoxic (Tc) cells.

Due to the identification of new tumor-specific antigens and realization that the immune system plays a critical role in the prevention of cancer and the control of tumor growth, in recent years, there has been a renewed interest in the development of therapeutic cancer vaccines (e.g., to reduce tumor burden and control metastasis).

The demonstration that in vivo engagement of NKT cells by their glycolipid ligand α-GalCer rapidly induces a cascade of cellular activation that involves elements common to innate and adaptive immunity as well as the generation of tumor-specific cytotoxic T cells (Nishimura et al., 2000, supra) suggests that α-GalCer administration may generally affect not only the speed and strength but also the type of subsequent immune responses, in particular, those directed against tumor cells. Indeed, Kabayashi et al. (1995, Oncol. Res., 7: 529-534) discovered that a synthetic form of α-GalCer (KRN 7000) had stronger antimetastatic activities in B 16-bearing mice than biological response modifiers such as OK432 and Lentinan and a chemotherapeutic agent Mitomycin C. In these experiments, 60% of mice bearing tumors were cured by treatment with 100 μg/kg KRN7000. KRN7000 was also shown to induce a pronounced tumor-specific immunity in mice with liver metastasis of murine T-lymphoma EL-4 cells (Nakagawa et al., Oncol. Res., 10: 561-568, 1998) or Colon26 cells (Nakagawa et al., Cancer Res., 58: 1202-1207, 1998). Furthermore, the administration of α-GalCer to mice was found to inhibit the development of hepatic metastasis of primary melanomas (Kawano et al., 1998, Proc. Natl. Acad. Sci. USA, 95: 5690-5693).

The data presented above have led the present inventors to a hypothesis that the glycosylceramide-induced NKT cell responses may also contribute to immune responses involved in combating various infections. Indeed, the present inventors and co-workers have recently observed that the administration of α-GalCer to mice resulted rapidly in strong anti-malaria activity, inhibiting the development of intra-hepatocytic stages of the rodent malaria parasites, P. yoeli and P. berghei (Gonzalez-Aseguinolaza et al., 2000, Proc. Natl. Acad. Sci. USA, 97: 8461-8466). The administration of α-GalCer alone to mice lacking either CD1d or Vα14 NKT cells, however, failed to protect them against malaria, indicating that the anti-malaria activity of α-GalCer requires both NKT cells and the expression of CD1d. Furthermore, α-GalCer was unable to inhibit parasite development in the liver of mice lacking either IFN-γ or the IFN-γ receptor, indicating that the anti-malaria activity of the glycolipid is primarily mediated by IFN-γ.

In light of the data on the NKT-mediated anti-tumor and anti-parasite activity of α-GalCer, it has been proposed that this glycolipid is a potent inducer of protective immune responses (see, e.g., Park and Bendelac, supra). The present inventors have significantly expanded these hypotheses by conceiving and demonstrating for the first time that α-GalCer and related glycosylceramides can be employed not just as antigens but also as adjuvants capable of enhancing and/or extending the duration of the protective immune responses induced by other antigens. This is an unexpected discovery, because α-GalCer-mediated NKT cell activation results in the complete elimination of malaria-infected cells, thus eliminating the source of antigen necessary for the development of an adaptive immune response. In fact, the administration of α-GalCer two days before immunization with irradiated sporozoites almost completely abolishes sporozoites-induced protection. Therefore, in order to use α-GalCer as an adjuvant, the timing of the administration in relation to the antigen given is very important.

Accordingly, the present invention provides for the first time methods and compositions for enhancing and/or extending the duration of the immune response against an antigen in a mammal, notably a human, involving the conjoint immunization of the mammal with (i) an antigen and (ii) an adjuvant comprising glycosylceramide, in particular, α-GalCer.

Importantly, in addition to its ability to stimulate immune responses, it has been demonstrated that α-GalCer, independently of its dosage, does not induce toxicity in rodents and monkeys (Nakagawa et al., 1998, Cancer Res., 58: 1202-1207). Moreover, although a recent study showed the transient elevation of liver enzyme activities immediately after α-GalCer treatment in mice, suggesting a minor liver injury (Osman et al., 2000, Eur. J. Immunol., 39: 1919-1928), human trials are currently being conducted using α-GalCer to treat cancer patients without a notable complication (Giaccone et al., 2000, Abstract. Proc. Amer. Soc. Clin. Oncol., 19: 477a). Finally, unlike many other newly developed adjuvants (see below), α-GalCer and related glycosylceramides can be produced synthetically with reasonable yields and efficiency (see, e.g., U.S. Pat. No. 5,936,076). All of these factors make glycosylceramides and, in particular α-GalCer, desirable adjuvant candidates.

In contrast to α-GalCer and related glycosylceramides, conventional vaccine delivery systems and the adjuvants approved for human use, aluminium salts and MF59 (Singh and O'Hagan, Nat. Biotechnol., 17: 1075-1081, 1999), are poor at inducing CD8+ T cell responses. Although certain novel adjuvants, such as purified saponins, immunostimulatory complexes, liposomes, CpG DNA motifs, and recombinant attenuated viruses (e.g., adenovirus, Sindbis virus, influenza virus, and vaccinia virus), have been shown to improve the antigen specific cellular immune responses over those induced by the same antigen given alone or in combination with standard alum adjuvants (Newman et al., J. Immunol., 1992; 148:2357-2362; Takahashi et al., Nature, 1990, 344: 873-875; Babu et al., Vaccine, 1995, 13:1669-1676; Powers et al., J. Infect. Dis., 1995, 172:1103-7; White et al., Vaccine, 1995, 13:1111-1122; Krieg et al., Trends Microbiol., 6: 23-27, 1998; Rodrigues et al., J. Immunol., 158: 1268-1274, 1997; Tsuji et al., J. Virol., 72: 6907-6910, 1998; Li et al., Proc. Natl. Acad. Sci. USA, 90: 5214-52188, 1993), none of the currently available adjuvants combine low toxicity in humans, cost-efficiency of production and the ability to efficiently stimulate the immune system.

The development of an adaptive immune response is a multifactorial phenomenon, in which many elements participate. In this regard, α-GalCer-activated NKT cells induce the activation of many of the elements involved in the development of the adaptive immune response, such as antigen presenting cells (APC), B cells, T helper (Th) cells and T cytotoxic (Tc) cells. Therefore, theoretically, α-GalCer could be an ideal immunomodulator. Additional advantage is that α-GalCer can be administered and activate the immune system via many different routes, including oral, subcutaneous, and intramuscular routes, which are suitable for human use. Finally, it has been shown that α-GalCer does not induce toxicity in rodents and monkeys (Nakagawa et al., Cancer Res., 58:1202-1207, 1998).

Accordingly, there is a great need in the art to develop new adjuvants that would combine low toxicity and easy availability with the ability to enhance and/or prolong the antigen-specific immune responses to a significant degree. The present invention addresses these and other needs in the art by providing glycosylceramides, a novel group of adjuvants with superior properties. Such adjuvants can improve prophylactic and/or therapeutic vaccines for the treatment of various infections and cancers.

SUMMARY OF THE INVENTION

An object of the present invention is to provide a method for augmenting an immunogenicity of an antigen in a mammal, comprising administering said antigen conjointly with an adjuvant composition comprising a glycosylceramide of the general Formula 1:

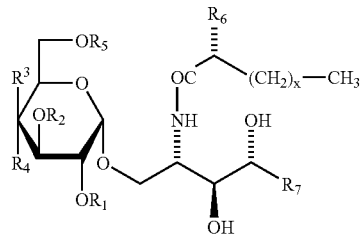

wherein $R_1$, $R_2$ and $R_5$ represent H or a specific monosaccharide; $R_3$ and $R_6$ represent H or OH, respectively; $R_4$ represents H, OH or a specific monosaccharide; X denotes an integer from 1 to 23; $R_7$ represents any one of the following groups (a)-(g): (a)—$(CH_2)_{11}$—$CH_3$, (b) —$(CH_2)_{12}$—$CH_3$, (c) —$(CH_2)_{13}$—$CH_3$, (d) —$(CH_2)_9$—$CH(CH_3)_2$, (e) —$(CH_2)_{10}$—$CH(CH_3)_2$, (f) —$(CH_2)_{11}$—$CH(CH_3)_2$, (g) —$(CH_2)_{11}$—$CH(CH_3)$—$C_2H_5$.

A preferred adjuvant of the present invention comprises α-galactosylceramide α-GalCer), specifically, (2S,3S,4R)-1—O-(α-D-galactopyranosyl)-2-(N-hexacosanoylamino)-1,3,4-octadecanetriol represented by the Formula 2:

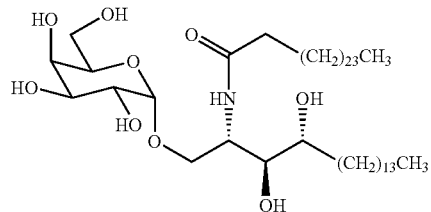

According to the present invention, the use of glycosylceramide as an adjuvant results in an enhancement and/or extension of the duration of the protective immunity induced by the antigen and is attributed at least in part to the enhancement and/or extension of antigen specific Th1-type responses, in particular, CD8+ T cell responses.

The glycosylceramide-containing adjuvant of the invention can be conjointly administered with any antigen, in particular, with antigens derived from infectious agents or tumors. Preferably, the adjuvant and antigen are administered simultaneously, most preferably in a single dosage form.

In a further embodiment, the invention provides a prophylactic and/or therapeutic method for treating a disease in a mammal comprising administering to said mammal an immunoprotective antigen together with an adjuvant composition that includes glycosyl-ceramide. As specified herein, this method can be useful for preventing and/or treating various infectious or neoplastic diseases. In a preferred embodiment, the method of the invention is employed to treat an infection selected from the group consisting of viral infection, bacterial infection, parasitic infection, and fungal infection.

Thus, in a specific embodiment, the present invention discloses a method for conferring immunity against the sporozoite stage of malaria in a mammal (e.g., human), wherein said method comprises conjointly administering to said mammal a malaria-specific antigen and an immunoadjuvant comprising α-GalCer. In another specific embodiment, the invention discloses a method for enhancing the immune response to HIV infection (and potentially preventing and/or treating AIDS) in a mammal, wherein said method comprises conjointly administering to said mammal an HIV-specific antigen and an adjuvant comprising α-GalCer. Additional specific methods disclosed herein include without limitation:

(i) enhancing the immune response to *Mycobacterium bovis* Bacillus Calmette-Guérin for prevention of *M. tuberculosis* infection, by administering *Mycobacterium bovis* Bacillus Calmette-Guérin and an adjuvant comprising α-GalCer;

(ii) enhancing the immune response to melanoma by administering a plasmid cDNA coding for the human melanoma-associated antigen, gp100, and an adjuvant comprising α-GalCer;

(iii) enhancing the immune response to *Candida albicans* by administering peptides derived from the immunodominant antigen, 65 kDa mannoprotein (MP65) and an adjuvant comprising α-GalCer.

In conjunction with the methods of the present invention, also provided are pharmaceutical and vaccine compositions comprising an immunogenically effective amount of an antigen and an immunogenically effective amount of an adjuvant selected from glycosyl-ceramides within Formula 1 as well as, optionally, a pharmaceutically acceptable carrier or excipient. In a specific embodiment, glycosylceramide used for the preparation of the adjuvant of the invention is α-GalCer, specifically [(2S,3S,4R)-1—O-(α-D-galactopyranosyl)-2-(N-hexacosanoylamino)-1,3,4-octadecanetriol].

The antigens useful in the compositions of the present invention include without limitation various viral, bacterial, fungal, parasite-specific, and tumor-specific antigens. Non-limiting examples of viral antigens of the invention include HIV antigens such as gp120, gp160, p18, Tat, Gag, Pol, Env, Nef; glycoprotein from Herpesvirus; surface antigen and core antigen from Hepatitis B virus. Non-limiting examples of bacterial antigens of the invention include OspA, OspB and OspC antigens from *Borrelia* sp. Non-limiting examples of fungal and parasite antigens of the invention include MP65 from *Candida albicans* and CS protein from Plasmodium sp., respectively. Non-limiting examples of tumor-specific antigens of the invention include Melan A and gp100 antigens from melanoma.

In a specific embodiment, the antigen is malaria-specific and comprises, for example, irradiated plasmodial sporozoites or a synthetic peptide antigen comprising a T cell epitope of the malarial circumsporozoite (CS) protein such as CD4+ T cell epitope YNRNIVNR LLGDALNGKPEEK (SEQ ID NO: 1) or CD8+ T cell epitope SYVPSAEQI (SEQ ID NO: 2) of *P. yoelii* CS protein, or CD4+ T cell epitope $(NVDPNANP)_n$ (SEQ ID NO: 3), or CD4+/CD8+ T cell epitope EYLNKIQNSLSTEWSPCSVT (SEQ ID NO: 4) of *P. falciparum* CS protein. In another preferred embodiment, the antigen is HIV-specific such as CD8+ T cell epitope RGPGRAFVTI (SEQ ID NO: 5) of p18 protein or HIV-1 Gag p24 CD8+ T cell epitopes (e.g., KAFSPEVIPMF (aa 30-40, SEQ ID NO: 6), KAFSPEVI (aa 30-37, SEQ ID NO: 7), TPQDLNM (or T) ML (aa 180-188, SEQ ID NOS: 8 and 9), DTINEEAAEW (aa 203-212, SEQ ID NO: 10), KRWIILGLNK (aa 263-272, SEQ ID NO: 11), and QATQEVKNW (aa 308-316, SEQ ID NO: 12)), or Gag p17 CD8+ T cell epitopes (e.g., RLRPGGKKK (aa 20-29, SEQ ID NO: 13) and SLYNTVATL (aa 77-85, SEQ ID NO: 14)).

In a specific embodiment, the antigen is presented by a recombinant virus expressing said antigen. Preferably, the virus is selected from the group consisting of a recombinant adenovirus, recombinant pox virus, and recombinant Sindbis virus.

The invention also provides a method for preparing a vaccine composition comprising at least one antigen and a glycosylceramide-containing adjuvant, said method comprising admixing the adjuvant and the antigen.

In a related embodiment, the present invention provides a kit for the preparation of a pharmaceutical or vaccine composition comprising at least one antigen and a glycosylceramide-containing adjuvant, said kit comprising the antigen in a first container, and the adjuvant in a second container, and optionally instructions for admixing the antigen and the adjuvant and/or for administration of the composition; and wherein optionally the containers are in a package.

BRIEF DESCRIPTION OF THE DRAWINGS

FIGS. 1A-D. α-GalCer enhances protective anti-malaria immunity induced by irradiated sporozoites and recombinant viruses expressing a plasmodial antigen. A. Groups of BALB/c mice were co-injected intraperitoneally with different doses of α-GalCer (0.5, 1, or 2 μg) or vehicle (−), together with intravenous immunization with *P. yoelii* irradiated sporozoites (γ-spz). Two weeks later all groups of mice were challenged with infective sporozoites, and the amount of parasite rRNA in the livers was measured by real time RT-PCR. Sera from immunized and non-immunized mice were collected and their titers of anti-sporozoite antibodies assayed by IFA. B. A single dose of α-GalCer was administered two days before (−2), the same day (0) or two days after (+2) immunization with (γ-spz into BALB/c (■) or B10. D2 (□) mice. C. A group of BALB/c mice was immunized subcutaneously with a recombinant adenovirus expressing the *P. yoelii* CS protein, AdPyCS, together with s.c. administration of α-GalCer (+) or vehicle (−). D. A group of BALB/c mice was immunized s.c. with a recombinant Sindbis virus expressing a CD8+T cell epitope of the *P. yoelii* CS protein, SIN(Mal), together with s.c. administration of α-GalCer (+) or vehicle (−). Asterisk (*) indicates a significant ($P<0.01$) difference between the two values using an unpaired t-test. In B-D, all groups of mice were infected with live *P. yoelii* sporozoites two weeks later, and the parasite burden in the liver was determined as described in A. Results are expressed as the mean values±SD of five mice.

FIGS. 2A-C. α-GalCer increases the level of antigen-specific T cell responses elicited by various vaccines. A. A group of BALB/c mice was immunized s.c. with γ-spz together with or without administration of α-GalCer by the same route, and two or six weeks later splenic lymphocytes were isolated and the number of IFN-γ secreting CS-specific CD8+ (■) and CD4+ (□) T cells was determined by an ELISPOT assay. B. A group of BALB/c mice was immunized s.c. with a recombinant adenovirus expressing the *P. yoelii* CS protein, AdPyCS, together with s.c. administration of α-GalCer (+) or vehicle (−). Two weeks later the number of IFN-γ secreting CS-specific CD8+(■) and CD4+ (□) T cells was determined by an ELISPOT assay. C. A group of BALB/c mice was immunized s.c. with a recombinant Sindbis virus expressing a CD8+ T cell epitope of the *P. yoelii* CS protein, SIN(Mal), or a recombinant Sindbis virus expressing a CD8+ T cell epitope of p18 protein of HIV, SIN(p18), together with s.c. administration of α-GalCer (+) or vehicle (−). Two weeks later the number of IFN-γ secreting CS-specific and p18-specific CD8+ T cells was determined by an ELISPOT assay.

The data represent one of two experiments with similar results and are expressed as the mean values±SD of three mice.

Figure 2B:
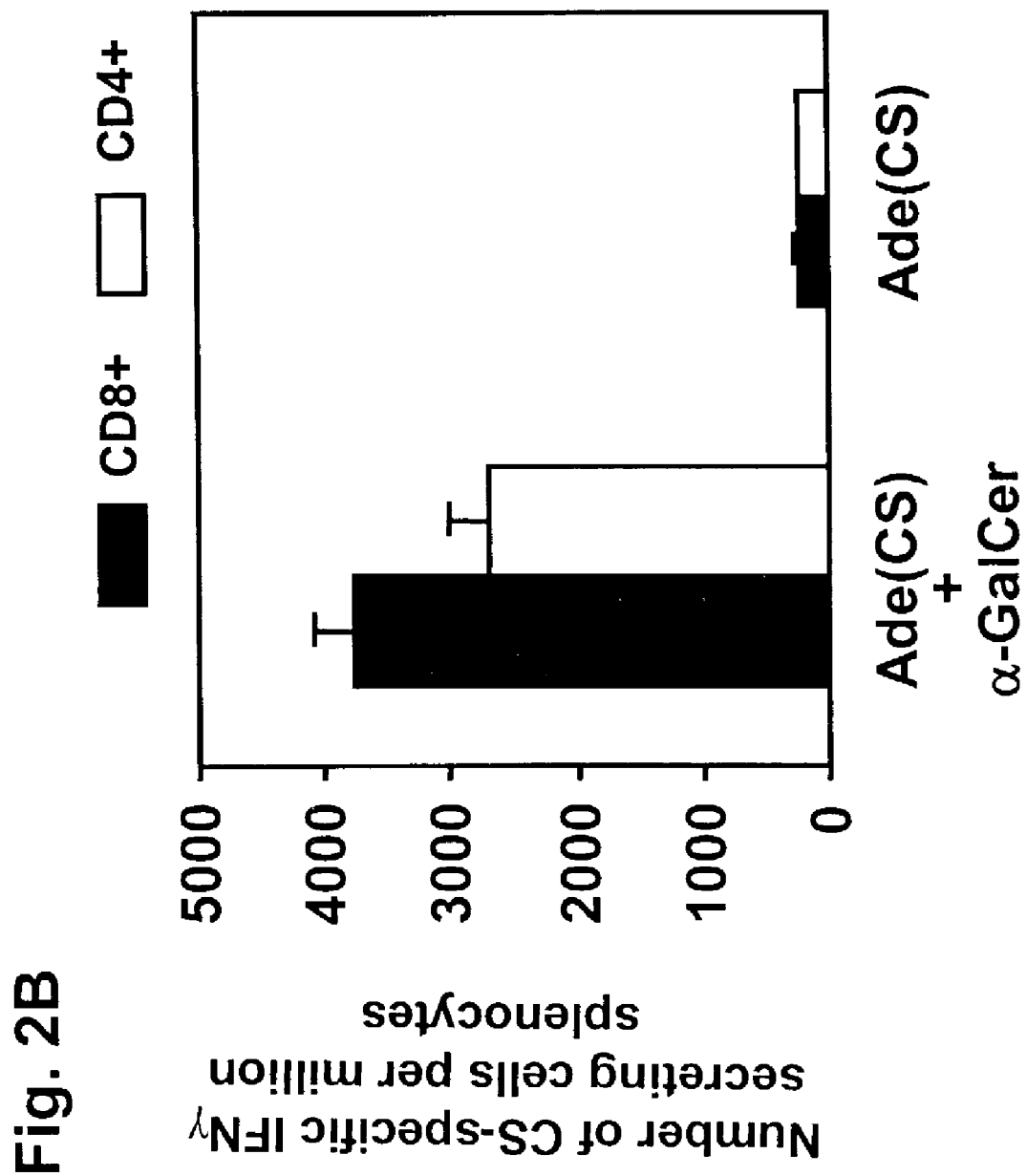
Figure 2C:
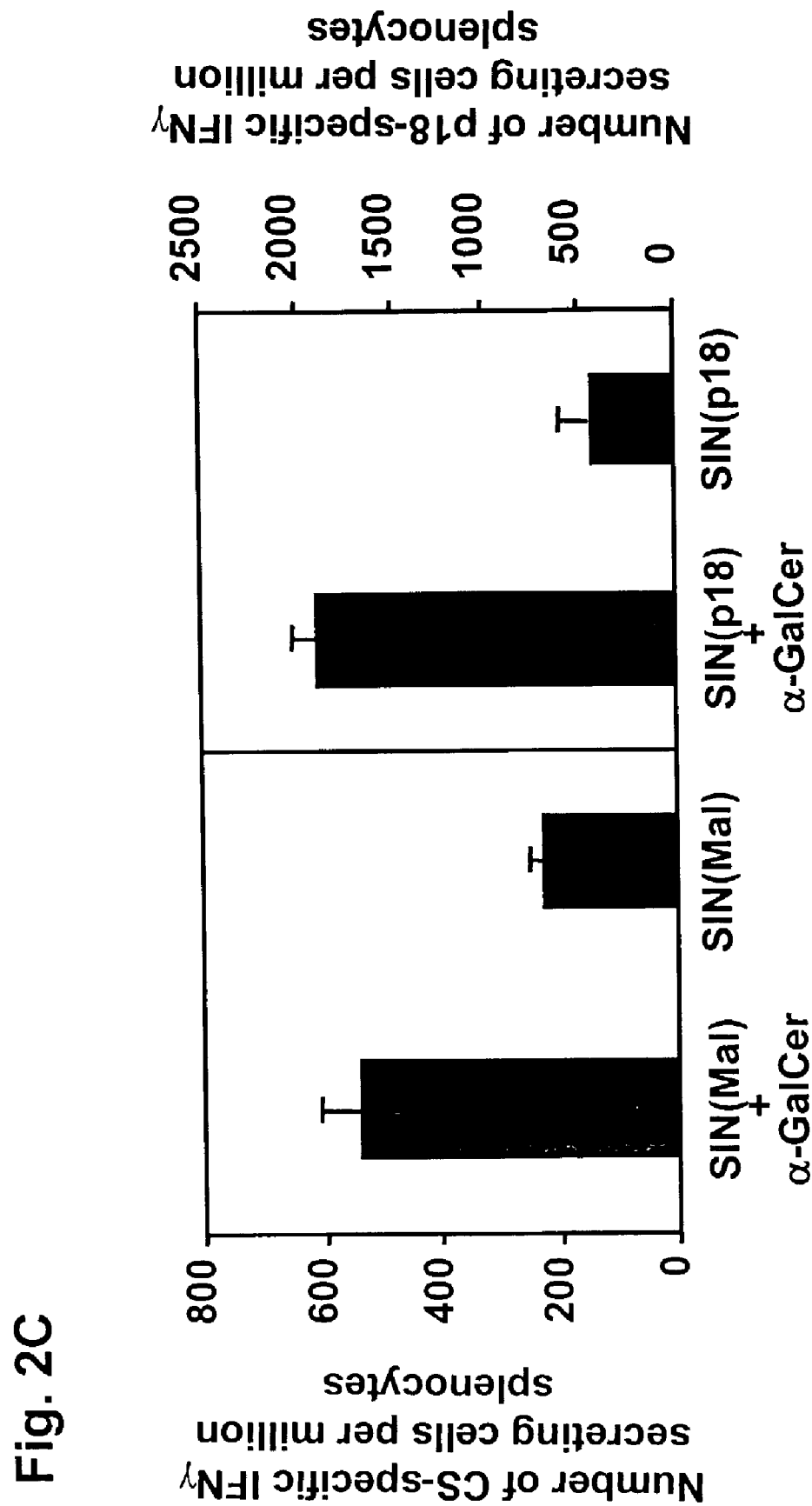
Figures 3A, 3B:
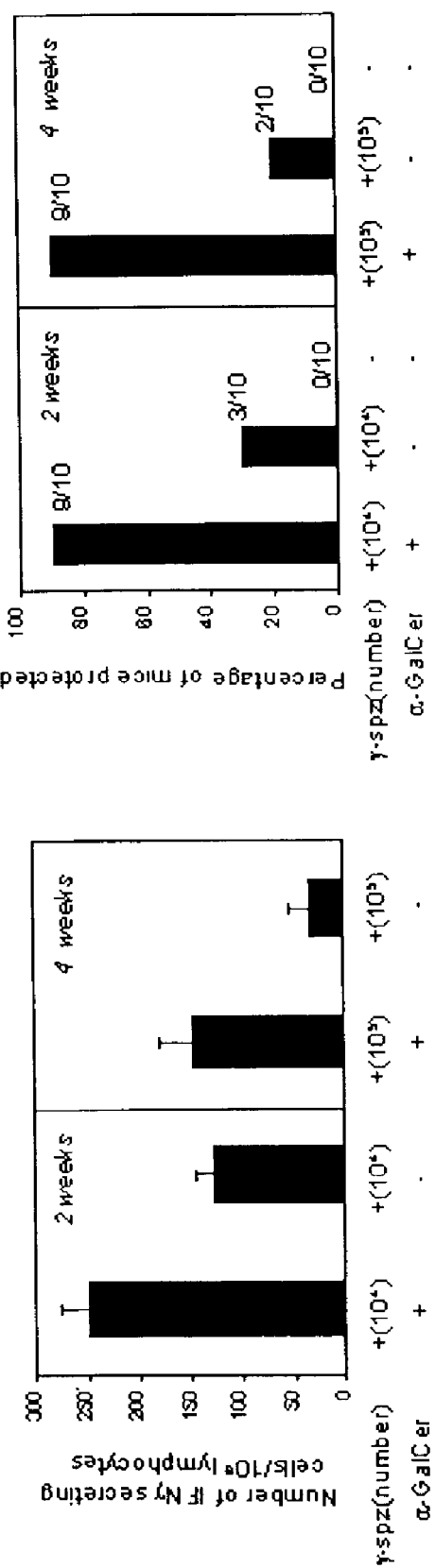

FIGS. 3A and 3B. α-GalCer prolongs the duration of the protective anti-malaria immune responses elicited by γ-spz. A. BALB/c mice were immunized with γ-spz together with α-GalCer (+) or vehicle (−), as in FIG. 2, and two to four weeks later the number of IFN-γ secreting CS-specific CD8+T cells in the spleens was determined by an ELISPOT assay. B. BALB/c mice treated with α-GalCer (+) or vehicle (−) were immunized with either $1\times10^4$ or $1\times10^5$ γ-spz, and two or four weeks later respectively, these plus non-immunized mice were challenged with 50 viable P. yoelii sporozoites. Occurrence of blood infection was determined by monitoring parasitemia in thin blood smears from days 3 to 14 after the challenge.

Figure 4A:
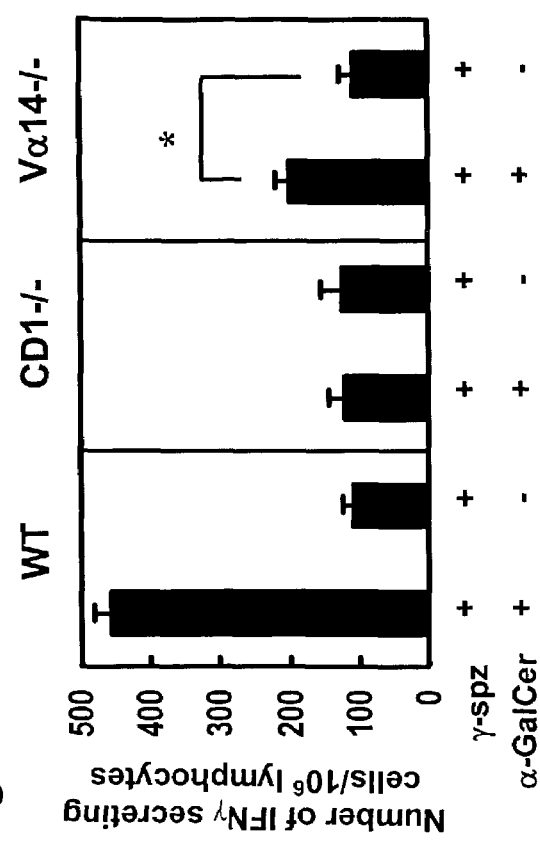
Figure 4B:
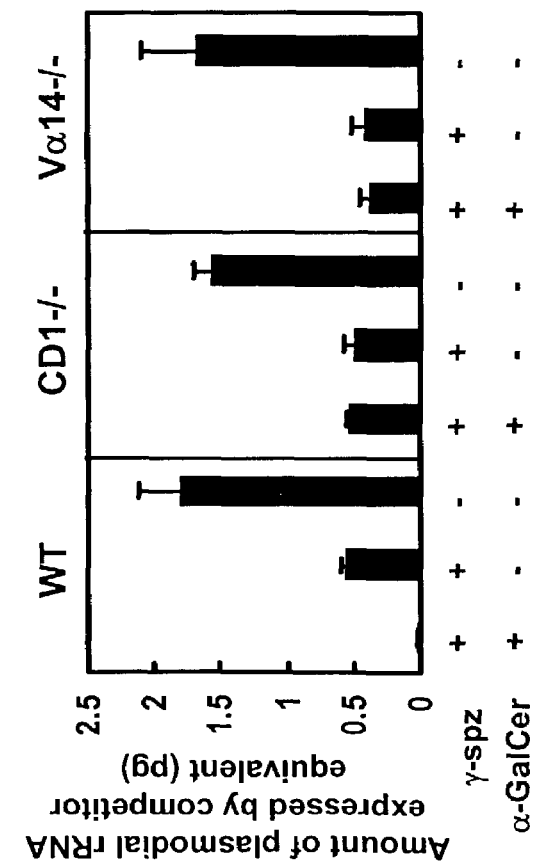

FIGS. 4A and 4B. The adjuvant activity of α-GalCer requires CD1d molecules and Vα14 NKT cells. A. Groups of CD1d-deficient (CD1$^{-/-}$), Vα14 NKT (Jα281$^{-/-}$) deficient and wild-type (WT) mice on a BALB/c background were immunized i.v. with γ-spz together with i.p. administration of α-GalCer (+) or vehicle (−). Two weeks later these and non-immunized mice were challenged with viable sporozoites, and the parasite burden in the liver was measured as described in FIG. 1. B. Identical groups of mice as described in A were immunized with γ-spz with i.p. injection of α-GalCer (+) or vehicle (−). Two weeks later the number of IFN-γ secreting CS-specific CD8+ T cells in the spleens was determined by an ELISPOT assay. Asterisk (*) indicates a significant (P<0.01) difference between the two values using an unpaired t-test. The results reflect two experiments with similar results and are expressed as the mean values±SD of five (A) or three (B) mice.

Figure 5A:
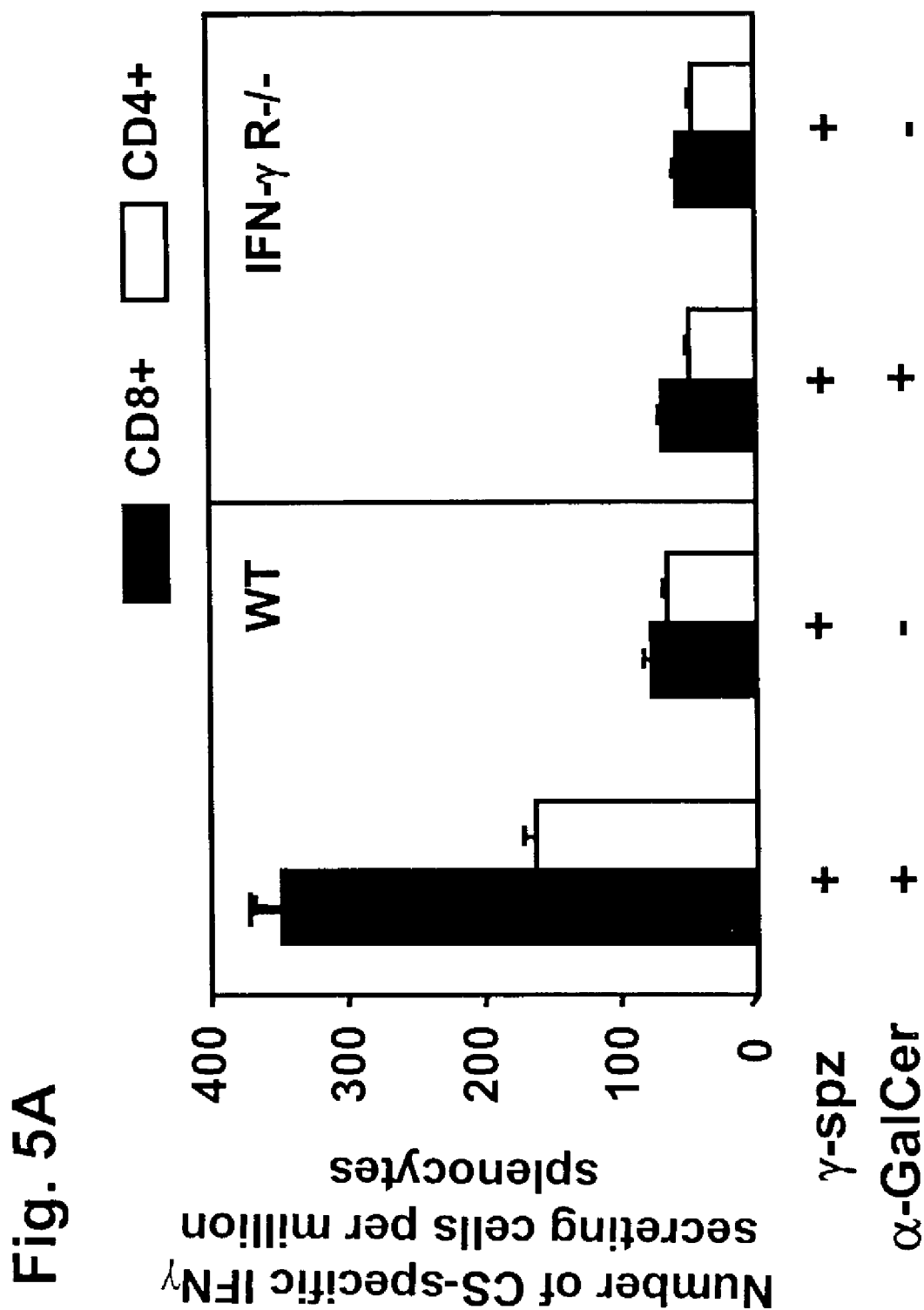

FIGS. 5A-C. The adjuvant activity of α-GalCer is abolished in IFN-γ receptor-deficient mice. A. Groups of IFN-γ receptor-deficient (IFN-γR$^{-/-}$) and wild-type (WT) mice on a B10.D2 background were immunized i.v. with γ-spz together with i.p. administration of α-GalCer (+) or vehicle (−). Two weeks later splenic lymphocytes were obtained and the number of IFN-γ secreting CS-specific CD8+ (■) and CD4+ (□) T cells were determined by an ELISPOT assay. B. Hepatic lymphocytes were obtained from IFN-γR$^{-/-}$ and WT mice and stained with PE-labeled CD1d/α-GalCer tetramer and FITC-labeled anti-CD3 antibody, and the percentage of α-GalCer-specific T cells was determined by flow cytometric analysis. The number indicated in the upper right corners represents the percentage of double-positive cells among the liver lymphoid cell population. C. Hepatic lymphocytes were obtained from IFN-γR$^{-/-}$ (■) or WT (□) mice, and the number of IFN-γ or IL-4 secreting α-GalCer-specific cells were determined by an ELISPOT assay. Results are expressed as the mean values±SD of five mice.

DETAILED DESCRIPTION OF THE INVENTION

Definitions

The terms "adjuvant" and "immunoadjuvant" are used interchangeably in the present invention and refer to a compound or mixture that may be non-immunogenic when administered to a host alone, but that augments the host's immune response to another antigen when administered conjointly with that antigen.

Adjuvant-mediated enhancement and/or extension of the duration of the immune response can be assessed by any method known in the art including without limitation one or more of the following: (i) an increase in the number of antibodies produced in response to immunization with the adjuvant/antigen combination versus those produced in response to immunization with the antigen alone; (ii) an increase in the number of T cells recognizing the antigen or the adjuvant; and (iii) an increase in the level of one or more Type I cytokines.

Adjuvants of the invention comprise compounds which belong to the class of sphingoglycolipids, specifically glycosylceramides, which can be represented by a general Formula 1:

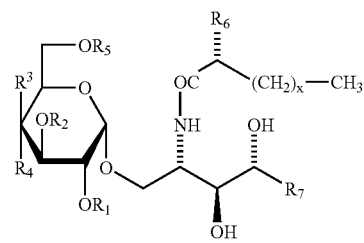

wherein $R_1$, $R_2$ and $R_5$ represent H or a specific monosaccharide; $R_3$ and $R_6$ represent H or OH, respectively; $R_4$ represents H, OH or a specific monosaccharide; X denotes an integer from 1 to 23; $R_7$ represents any one of the following groups (a)-(g): (a) —(CH$_2$)$_{11}$—CH$_3$, (b) —(CH$_2$)$_{12}$—CH$_3$, (c) —(CH$_2$)$_{13}$—CH$_3$, (d) —(CH$_2$)$_9$—CH(CH$_3$)$_2$, (e) —(CH$_2$)$_{10}$—CH(CH$_3$)$_2$, (f) —(CH$_2$)$_{11}$—CH(CH$_3$)$_2$, (g) —(CH$_2$)$_{11}$—CH(CH$_3$)—C$_2$H$_5$.

A preferred adjuvant of the present invention comprises α-galactosylceramide (α-GalCer), specifically, (2S,3S,4R)-1—O-(α-D-galactopyranosyl)-2-(N-hexacosanoylamino)-1,3,4-octadecanetriol represented by the Formula 2:

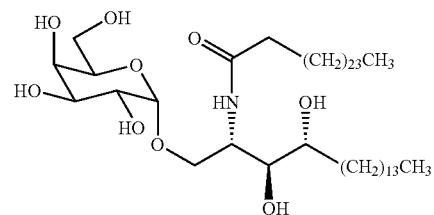

Other examples of glycosylceramides useful in adjuvants of the present invention include, without limitation:

α-glucosylceramide (α-GlcCer), specifically (2S,3S,4R)-1—O-(α-D-glucopyranosyl)-N-hexacosanoyl-2-amino-1,3,4-octadecanetriol, of the Formula 3:

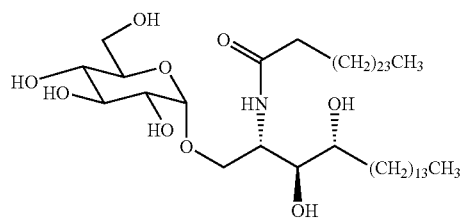

Galα1-6Galα1-1'Cer, specifically (2S,3S,4R)-2-amino-1—O-(α-D-galactopyranosyl-(1-6)-α-D-galactopyranosyl)-N-hexacosanoyl-1,3,4-octadecanetriol, of the Formula 4:

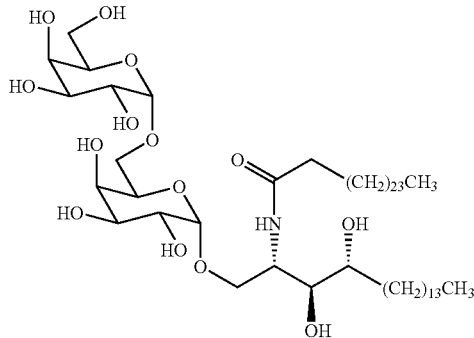

Galα1-6Glcα1-1'Cer, specifically (2S,3S,4R)-2-amino-1-O-(α-D-galactopyranosyl-(1-6)-α-D-glucopyranosyl)-N-hexacosanoyl-1,3,4-octadecanetriol, of the Formula 5:

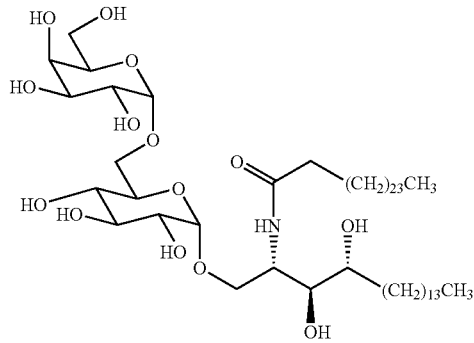

Galα1-2Glcα1-1'Cer, specifically (2S,3S,4R)-2-amino-1-O-(α-D-glucopyranosyl-(1-2)-α-D-galactopyranosyl)-N-[(R)-2-hydroxytetracosanoyl]-1,3,4-octadecanetriol, of the Fo

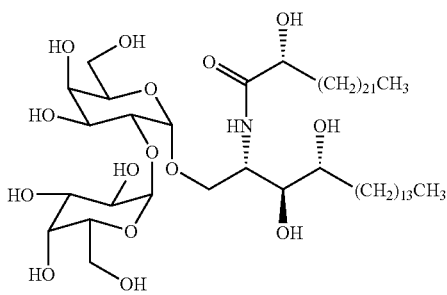

Galβ1-3Galα1-1'Cer, specifically (2S,3S,4R)-2-amino-1-O-(β-D-galactofuranosyl-(1-4)-α-D-galactopyranosyl)-N-[(R)-2-hydroxytetracosanoyl]-1,3,4-octadecanetriol, of the

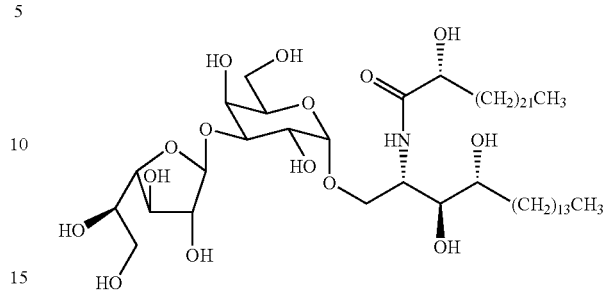

Preferably, the adjuvant of the invention is pharmaceutically acceptable for use in humans.

The adjuvant of the invention can be administered as part of a pharmaceutical or vaccine composition comprising an antigen or as a separate formulation, which is administered conjointly with a second composition containing an antigen. In any of these compositions glycosylceramide can be combined with other adjuvants and/or excipients/carriers. These other adjuvants include, but are not limited to, oil-emulsion and emulsifier-based adjuvants such as complete Freund's adjuvant, incomplete Freund's adjuvant, MF59, or SAF; mineral gels such as aluminum hydroxide (alum), aluminum phosphate or calcium phosphate; microbially-derived adjuvants such as cholera toxin (CT), pertussis toxin, *Escherichia coli* heat-labile toxin (LT), mutant toxins (e.g., LTK63 or LTR72), Bacille Calmette-Guerin (BCG), *Corynebacterium parvum*, DNA CpG motifs, muramyl dipeptide, or monophosphoryl lipid A; particulate adjuvants such as immunostimulatory complexes (ISCOMs), liposomes, biodegradable microspheres, or saponins (e.g., QS-21); cytokines such as IFN-γ, IL-2, IL-12 or GM-CSF; synthetic adjuvants such as nonionic block copolymers, muramyl peptide analogues (e.g., N-acetyl-muramyl-L-threonyl-D-isoglutamine [thr-MDP], N-acetyl-nor-muramyl-L-alanyl-D-isoglutamine, N-acetylmuramyl-L-alanyl-D-isoglutaminyl-L-alanine-2-[1'-2'-dipalmitoyl-sn-glycero-3-hydroxyphosphoryloxy]-ethylamine), polyphosphazenes, or synthetic polynucleotides, and surface active substances such as lysolecithin, pluronic polyols, polyanions, peptides, hydrocarbon emulsions, or keyhole limpet hemocyanins (KLH). Preferably, these additional adjuvants are also pharmaceutically acceptable for use in humans.

Within the meaning of the present invention, the term "conjoint administration" is used to refer to administration of an immune adjuvant and an antigen simultaneously in one composition, or simultaneously in different compositions, or sequentially. For the sequential administration to be considered "conjoint", however, the antigen and adjuvant must be administered separated by a time interval that still permits the adjuvant to augment the immune response to the antigen. For example, when the antigen is a polypeptide, the antigen and adjuvant are administered on the same day, preferably within an hour of each other, and most preferably simultaneously. However, when nucleic acid is delivered to the subject and the polypeptide antigen is expressed in the subject's cells, the adjuvant is administered within 24 hours of nucleic acid administration, preferably within 6 hours.

As used herein, the term "immunogenic" means that an agent is capable of eliciting a humoral or cellular immune response, and preferably both. An immunogenic entity is also antigenic. An immunogenic composition is a composition that elicits a humoral or cellular immune response, or both, when administered to an animal having an immune system.

The term "antigen" refers to any agent (e.g., protein, peptide, polysaccharide, glycoprotein, glycolipid, nucleic acid, or combination thereof) that, when introduced into a host, animal or human, having an immune system (directly or upon expression as in, e.g., DNA vaccines), is recognized by the immune system of the host and is capable of eliciting an immune response. As defined herein, the antigen-induced immune response can be humoral or cell-mediated, or both. An agent is termed "antigenic" when it is capable of specifically interacting with an antigen recognition molecule of the immune system, such as an immunoglobulin (antibody) or T cell antigen receptor (TCR). Within the meaning of the present invention, the antigens are preferably "surface antigens", i.e., expressed naturally on the surface of a pathogen, or the surface of an infected cell, or the surface of a tumor cell. A molecule that is antigenic need not be itself immunogenic, i.e., capable of eliciting an immune response without an adjuvant or carrier.

The term "epitope" or "antigenic determinant" refers to any portion of an antigen recognized either by B cells, or T cells, or both. Preferably, interaction of such epitope with an antigen recognition site of an immunoglobulin (antibody) or T cell antigen receptor (TCR) leads to the induction of antigen-specific immune response. T cells recognize proteins only when they have been cleaved into smaller peptides and are presented in a complex called the "major histocompatability complex (MHC)" located on another cell's surface. There are two classes of MHC complexes-class I and class II, and each class is made up of many different alleles. Class I MHC complexes are found on virtually every cell and present peptides from proteins produced inside the cell. Thus, class I MHC complexes are useful for killing cells infected by viruses or cells which have become cancerous as the result of expression of an oncogene. T cells which have a protein called CD8 on their surface, bind specifically to the MHC class I/peptide complexes via the T cell receptor (TCR). This leads to cytolytic effector activities. Class II MHC complexes are found only on antigen-presenting cells (APC) and are used to present peptides from circulating pathogens which have been endocytosed by APCs. T cells which have a protein called CD4 bind to the MHC class II/peptide complexes via TCR. This leads to the synthesis of specific cytokines which stimulate an immune response. To be effectively recognized by the immune system via MHC class I presentation, an antigenic polypeptide has to contain an epitope of at least about 8 to 10 amino acids, while to be effectively recognized by the immune system via MHC class II presentation, an antigenic polypeptide has to contain an epitope of at least about 13 to 25 amino acids. See, e.g., *Fundamental Immunology*, $3^{rd}$ Edition, W. E. Paul ed., 1999, Lippincott-Raven Publ.

The term "species-specific" antigen refers to an antigen that is only present in or derived from a particular species. Thus, the term "malaria-derived" or "malaria-specific" antigen refers to a natural (e.g., irradiated sporozoites) or synthetic (e.g., chemically produced multiple antigen peptide [MAP] or recombinantly synthesized polypeptide) antigen comprising at least one epitope (B cell and/or T cell) derived from any one of the proteins constituting plasmodium (said plasmodium being without limitation *P. falciparum, P. vivax, P. malariae, P. ovale, P. reichenowi, P. knowlesi, P. cynomolgi, P. brasilianum, P. yoelii, P. berghei, or P. chabaudi*) and comprising at least 5-10 amino acid residues. A preferred plasmodial protein for antigen generation is circumsporozoite (CS) protein, however, other proteins can be also used, e.g., Thrombospondin Related Adhesion (Anonymous) protein (TRAP), also called Sporozoite Surface Protein 2 (SSP2), LSA I, hsp70, SALSA, STARP, Hep17, MSA, RAP-1, RAP-2, etc.

The term "vaccine" refers to a composition (e.g., protein or vector such as, e.g., an adenoviral vector, Sindbis virus vector, or pox virus vector) that can be used to elicit protective immunity in a recipient. It should be noted that to be effective, a vaccine of the invention can elicit immunity in a portion of the immunized population, as some individuals may fail to mount a robust or protective immune response, or, in some cases, any immune response. This inability may stem from the individual's genetic background or because of an immunodeficiency condition (either acquired or congenital) or immunosuppression (e.g., due to treatment with chemotherapy or use of immunosuppressive drugs, e.g., to prevent organ rejection or suppress an autoimmune condition). Vaccine efficacy can be established in animal models.

The term "DNA vaccine" is an informal term of art, and is used herein to refer to a vaccine delivered by means of a recombinant vector. An alternative, and more descriptive term used herein is "vector vaccine" (since some potential vectors, such as retroviruses and lentiviruses are RNA viruses, and since in some instances non-viral RNA instead of DNA is delivered to cells through the vector). Generally, the vector is administered in vivo, but ex vivo transduction of appropriate antigen presenting cells, such as dendritic cells (DC), with administration of the transduced cells in vivo, is also contemplated.

The term "treat" is used herein to mean to relieve or alleviate at least one symptom of a disease in a subject. Within the meaning of the present invention, the term "treat" may also mean to prolong the prepatency, i.e., the period between infection and clinical manifestation of a disease. Preferably, the disease is either infectious disease (e.g., viral, bacterial, parasitic, or fungal) or malignancy (e.g., solid or blood tumors such as sarcomas, carcinomas, gliomas, blastomas, pancreatic cancer, breast cancer, ovarian cancer, prostate cancer, lymphoma, leukemia, melanoma, etc.).

The term "protect" is used herein to mean prevent or treat, or both, as appropriate, development or continuance of a disease in a subject. Within the meaning of the present invention, the disease is selected from the group consisting of infection (e.g., viral, bacterial, parasitic, or fungal) and malignancy (e.g., solid or blood tumors such as sarcomas, carcinomas, gliomas, blastomas, pancreatic cancer, breast cancer, ovarian cancer, prostate cancer, lymphoma, leukemia, melanoma, etc.). For example, as disclosed herein, a prophylactic administration of an anti-malarial vaccine comprising a plasmodium-derived antigen in combination with an adjuvant comprising α-GalCer can protect a recipient subject at risk of developing malaria. Similarly, according to the present invention, a therapeutic administration of a tumor-specific antigen conjointly with an adjuvant comprising a-GalCer or another glycosylceramide of Formula 1 can enhance an anti-tumor immune response leading to slow-down in tumor growth and metastasis or even tumor regression.

The term "protective immunity" refers to an immune response in a host animal (either active/acquired or passive/innate, or both) which leads to inactivation and/or reduction in the load of said antigen and to generation of long-lasting immunity (that is acquired, e.g., through production of antibodies), which prevents or delays the development of a disease upon repeated exposure to the same or a related antigen. A "protective immune response" comprises a humoral (antibody) immunity or cellular immunity, or both, effective to, e.g., eliminate or reduce the load of a pathogen or infected cell (or produce any other measurable alleviation of the infection), or to reduce a tumor burden in an immunized (vaccinated) subject. Within the meaning of the present invention, protective immunity may be partial.

Immune systems are classified into two general systems, the "innate" or "natural" immune system and the "acquired" or "adaptive" immune system. It is thought that the innate immune system initially keeps the infection under control, allowing time for the adaptive immune system to develop an appropriate response. Recent studies have suggested that the various components of the innate immune system trigger and augment the components of the adaptive immune system, including antigen-specific B and T lymphocytes (Fearon and Locksley, supra; Kos, 1998, Immunol. Res., 17: 303; Romagnani, 1992, Immunol. Today, 13: 379; Banchereau and Steinman, 1988, Nature, 392: 245).

The term "innate immunity" or "natural immunity" refers to innate immune responses that are not affected by prior contact with the antigen. Cells of the innate immune system, including macrophages and dendritic cells (DC), take up foreign antigens through pattern recognition receptors, combine peptide fragments of these antigens with MHC class I and class II molecules, and stimulate naive $CD8^+$ and $CD4^+$ T cells respectively (Banchereau and Steinman, supra; Holmskov et al., 1994, Immunol. Today, 15: 67; Ulevitch and Tobias, 1995, Annu. Rev. Immunol., 13: 437). Professional antigen-presenting cells (APC) communicate with these T cells leading to the differentiation of naive $CD4^+$ T cells into T-helper 1 (Th1) or T-helper 2 (Th2) lymphocytes that mediate cellular and humoral immunity, respectively (Trinchieri, 1995, Annu. Rev. Immunol., 13: 251; Howard and O'Garra, 1992, Immunol. Today, 13: 198; Abbas et al., 1996, Nature, 383: 787; Okamura et al., 1998, Adv. Immunol., 70: 281; Mosmann and Sad, 1996, Immunol. Today, 17: 138; O'Garra, 1998, Immunity, 8: 275).

The term "acquired immunity" or "adaptive immunity" is used herein to mean active or passive, humoral or cellular immunity that is established during the life of an animal, is specific for the inducing antigen, and is marked by an enhanced response on repeated encounters with said antigen. A key feature of the T lymphocytes of the adaptive immune system is their ability to detect minute concentrations of pathogen-derived peptides presented by MHC molecules on the cell surface.

As used herein, the term "augment the immune response" means enhancing or extending the duration of the immune response, or both. When referred to a property of an agent (e.g., adjuvant), the term "[able to] augment the immunogenicity" refers to the ability to enhance the immunogenicity of an antigen or the ability to extend the duration of the immune response to an antigen, or both.

The phrase "enhance immune response" within the meaning of the present invention refers to the property or process of increasing the scale and/or efficiency of immunoreactivity to a given antigen, said immunoreactivity being either humoral or cellular immunity, or both. An immune response is believed to be enhanced, if any measurable parameter of antigen-specific immunoreactivity (e.g., antibody titer, T cell production) is increased at least two-fold, preferably ten-fold, most preferably thirty-fold.

The term "therapeutically effective" applied to dose or amount refers to that quantity of a compound or pharmaceutical composition or vaccine that is sufficient to result in a desired activity upon administration to a mammal in need thereof. As used herein with respect to adjuvant—and antigen-containing compositions or vaccines, the term "therapeutically effective amount/dose" is used interchangeably with the term "immunogenically effective amount/dose" and refers to the amount/dose of a compound (e.g., an antigen and/or an adjuvant comprising glycosylceramide) or pharmaceutical composition or vaccine that is sufficient to produce an effective immune response upon administration to a mammal.

The phrase "pharmaceutically acceptable", as used in connection with compositions of the invention, refers to molecular entities and other ingredients of such compositions that are physiologically tolerable and do not typically produce untoward reactions when administered to a human. Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

The term "carrier" applied to pharmaceutical or vaccine compositions of the invention refers to a diluent, excipient, or vehicle with which a compound (e.g., an antigen and/or an adjuvant comprising glycosylceramide) is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution, saline solutions, and aqueous dextrose and glycerol solutions are preferably employed as carriers, particularly for injectable solutions. Suitable pharmaceutical carriers are described in "Remington's Pharmaceutical Sciences" by E. W. Martin, $18^{th}$ Edition.

The term "native antibodies" or "immunoglobulins" refers to usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain (VL) at one end and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., J Mol. Biol., 186: 651-663, 1985; Novotny and Haber, Proc. Natl. Acad. Sci. USA, 82: 4592-4596, 1985).

The term "antibody" or "Ab" is used in the broadest sense and specifically covers not only native antibodies but also single monoclonal antibodies (including agonist and antagonist antibodies), antibody compositions with polyepitopic specificity, as well as antibody fragments (e.g., Fab, F(ab')2, scFv and Fv), so long as they exhibit the desired biological activity.

"Cytokine" is a generic term for a group of proteins released by one cell population which act on another cell population as intercellular mediators. Examples of such cytokines are lymphokines, monokines, and traditional polypeptide hormones. Included among the cytokines are interferons (IFN, notably IFN-γ), interleukins (IL, notably IL-1, IL-2, IL-4, IL-10, IL-12), colony stimulating factors (CSF), thrombopoietin (TPO), erythropoietin (EPO), leukemia inhibitory factor (LIF), kit-ligand, growth hormones (GH), insulin-like growth factors (IGF), parathyroid hormone, thyroxine, insulin, relaxin, follicle stimulating hormone (FSH), thyroid stimulating hormone (TSH), leutinizing hormone (LH), hematopoietic growth factor, hepatic growth factor, fibroblast growth factors (FGF), prolactin, placental lactogen, tumor necrosis factors (TNF), mullerian-inhibiting substance, mouse gonadotropin-associated peptide, inhibin, activin, vascular endothelial growth factor (VEGF), integrin, nerve growth factors (NGF), platelet growth factor, transforming growth factors (TGF), osteoinductive factors, etc.

The term "subject" as used herein refers to an animal having an immune system, preferably a mammal (e.g., rodent such as mouse). In particular, the term refers to humans.

The term "about" or "approximately" usually means within 20%, more preferably within 10%, and most preferably still within 5% of a given value or range. Alternatively, especially in biological systems (e.g., when measuring an immune response), the term "about" means within about a log (i.e., an order of magnitude) preferably within a factor of two of a given value.

The terms "vector", "cloning vector", and "expression vector" mean the vehicle by which a DNA or RNA sequence (e.g., a foreign gene) can be introduced into a host cell, so as to transform the host and promote expression (e.g., transcription and/or translation) of the introduced sequence. Vectors include plasmids, phages, viruses, etc.

In accordance with the present invention there may be employed conventional molecular biology, microbiology, and recombinant DNA techniques within the skill of the art. Such techniques are well-known and are explained fully in the literature. See, e.g., Sambrook, Fritsch and Maniatis, *Molecular Cloning: A Laboratory Manual*, Second Edition (1989) Cold Spring Harbor Laboratory Press, Cold Spring Harbor, New York (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

A "nucleic acid molecule" (or alternatively "nucleic acid") refers to the phosphate ester polymeric form of ribonucleosides (adenosine, guanosine, uridine, or cytidine: "RNA molecules") or deoxyribonucleosides (deoxyadenosine, deoxyguanosine, deoxythymidine, or deoxycytidine: "DNA molecules"), or any phosphoester analogs thereof, such as phosphorothioates and thioesters, in either single stranded form, or a double-stranded helix. Oligonucleotides (having fewer than 100 nucleotide constituent units) or polynucleotides are included within the defined term as well as double stranded DNA-DNA, DNA-RNA, and RNA-RNA helices. This term, for instance, includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

As used herein, the term "polypeptide" refers to an amino acid-based polymer, which can be encoded by a nucleic acid or prepared synthetically. Polypeptides can be proteins, protein fragments, chimeric proteins, etc. Generally, the term "protein" refers to a polypeptide expressed endogenously in a cell. Generally, a DNA sequence encoding a particular protein or enzyme is "transcribed" into a corresponding sequence of mRNA. The mRNA sequence is, in turn, "translated" into the sequence of amino acids which form a protein. An "amino acid sequence" is any chain of two or more amino acids. The term "peptide" is usually used for amino acid-based polymers having fewer than 100 amino acid constituent units, whereas the term "polypeptide" is reserved for polymers having at least 100 such units. Herein, however, "polypeptide" will be the generic term.

Uses of Adjuvants Comprising Glycosylceramides

In one aspect, the present invention provides a method for augmenting an immunogenicity of an antigen in a mammal, comprising administering said antigen conjointly with an adjuvant composition comprising a glycosylceramide of Formula 1, preferably α-galactosyl-ceramide (α-GalCer). According to the present invention, the use of glycosylceramide as an adjuvant results in an enhancement and/or extension of the duration of the protective immunity induced by the antigen. For example, as disclosed herein, conjoint administration of glycosylceramide with peptides corresponding to T cell or B cell epitopes of tumor or viral antigens, or DNA constructs expressing these antigens enhances antigen-specific immune responses.

The glycosylceramide-containing adjuvant of the invention can be conjointly administered with any antigen, in particular, with antigens derived from infectious agents or tumors.

As discussed in the Background Section, the immunostimulating effects of glycosylceramides both in mice and humans depend on the expression of CD1d molecules and are mediated by NKT cells. Indeed, the instant invention demonstrates that α-GalCer adjuvant activity is attributed at least in part to its ability to enhance and/or extend NKT-mediated antigen-specific Th1-type T cell responses and CD8+ T cell (or Tc) responses.

From an immunotherapy view point, glycosylceramide-mediated activation of the NKT cell system appears to have distinct advantages over the other mechanisms for the following reasons: (a) the level of cytotoxicity of activated NKT cells is very high and effective against a wide variety of tumor cells or infected cells; (b) the activation of NKT cells by glycosylceramide is totally dependent on a CD1d molecule, which is monomorphic among individuals (Porcelli, Adv. Immunol., 59: 1-98, 1995), indicating that glycosylceramide-containing adjuvants can be utilized by all patients, regardless of MHC haplotype; (c) antigen-presenting functions of DC and NKT activation of human patients can be evaluated before immunotherapy by the in vivo assays in mice using Vα14 NKT cell status as an indicator.

According to the present invention, an adjuvant comprising glycosylceramide of Formula 1 and antigen can be administered either as two separate formulations or as part of the same composition. If administered separately, the adjuvant and antigen can be administered either sequentially or simultaneously. As disclosed herein, simultaneous administration of glycosylceramide adjuvant with the antigen is preferred and generally allows to achieve the most efficient immunostimulation.

As the glycosylceramide adjuvant of the invention exerts its immunostimulatory activity in combination with a plurality of different antigens, it is therefore useful for both preventive and therapeutic applications. Accordingly, in a further aspect, the invention provides a prophylactic and/or therapeutic method for treating a disease in a mammal comprising conjointly administering to said mammal an antigen and an adjuvant comprising a glycosyl-ceramide of Formula 1. This method can be useful, e.g., for protecting against and/or treating various infections as well as for treating various neoplastic diseases.

Immunogenicity enhancing methods of the invention can be used to combat infections, which include, but are not limited to, parasitic infections (such as those caused by plasmodial species, etc.), viral infections (such as those caused by influenza viruses, leukemia viruses, immunodeficiency viruses such as HIV, papilloma viruses, herpes virus, hepatitis viruses, measles virus, poxviruses, mumps virus, cytomegalovirus [CMV], Epstein-Barr virus, etc.), bacterial infections (such as those caused by *staphylococcus, streptococcus, pneumococcus, Neisseria gonorrhea, Borrelia, pseudomonas*, etc.), and fungal infections (such as those caused by *candida, trichophyton, ptyrosporum*, etc.).

Methods of the invention are also useful in treatment of various cancers, which include without limitation fibrosarcoma, myxosarcoma, liposarcoma, chondrosarcoma, osteogenic sarcoma, chordoma, angiosarcoma, endotheliosarcoma, lymphangiosarcoma, lymphangioendothelio-sarcoma, synovioma, mesothelioma, Ewing's tumor, leiomyosarcoma, rhabdomyosarcoma, colon carcinoma, pancreatic cancer, breast cancer, ovarian cancer, prostate cancer, lymphoma, leukemia, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

As further disclosed herein, maximal efficiency of the immunogenicity enhancing methods of present invention is attained when an antigen and glycosylceramide adjuvant are administered simultaneously.

In a specific embodiment, the present invention discloses a method for preventing and/or treating malaria in a mammal (e.g., human), wherein said method comprises conjointly administering to said mammal a malaria-specific antigen and an adjuvant comprising a glycosylceramide of Formula 1, preferably, α-GalCer. As disclosed in Example 1, infra, the immunization of mice with a sub-optimal dose of irradiated malaria parasites, co-administered with α-GalCer, greatly enhances protective anti-malaria immunity. The α-GalCer co-administration not only increases the level of protection but also prolongs the duration of protective anti-malaria immunity. Furthermore, it is disclosed herein that co-injection of mice with α-GalCer and irradiated parasites or peptides (corresponding to CD4+ or CD8+ epitopes of the malarial CS protein), leads to an increase in the number of antigen-specific T cells.

In another specific embodiment, the invention discloses a method for enhancing the immune response to HIV infection (and potentially preventing and/or treating AIDS) in a mammal, wherein said method comprises conjointly administering to said mammal an HIV-specific antigen and an α-GalCer adjuvant. As disclosed in Example 2, infra, co-administration of α-GalCer to mice immunized with a CD8+ T cell epitope (RGPGRAFVTI [SEQ ID NO: 5]) of p18 (V3 loop) of HIV, enhances almost 3 times the level of HIV-specific CD8+ T cell response compared to that induced in mice immunized without α-GalCer treatment.

The methods of the invention can be used in conjunction with other treatments. For example, an anti-cancer treatment using tumor-specific antigen and glycosylceramide-containing adjuvant of the present invention can be used in combination with chemotherapy and/or radiotherapy and/or IL-12 treatment. Anti-viral vaccines comprising α-glycosyl-ceramide-containing adjuvant can be used in combination with IFN-α treatment.

In addition to its therapeutic applications, the glycosylceramide adjuvant of the invention may be also applied as a research tool to the study of many aspects of basic immunology. For example, it can be used to study immune mechanisms, such as function of NKT cells, antigen presentation by DC, and modulation of immune responses by cytokines and their receptors. Glycosylceramide adjuvant can be also employed in vaccine design research, which could assist in identifying the requirements for protective immunity, since for the same antigen different adjuvants may produce immune responses of varying intensity and/or length.

Glycosylceramide-Containing Pharmaceutical and Vaccine Compositions

In conjunction with the methods of the present invention, also provided are pharmaceutical and vaccine compositions comprising an immunogenically effective amount of an antigen and immunogenically effective amount of an adjuvant comprising glycosylceramide as well as, optionally, an additional immunostimulant, carrier or excipient (preferably all pharmaceutically acceptable). Said antigen and adjuvant can be either formulated as a single composition or as two separate compositions, which can be administered simultaneously or sequentially.

Adjuvants of the invention comprise compounds which belong to the class of sphingoglycolipids, specifically glycosylceramides, which can be represented by a general Formula 1:

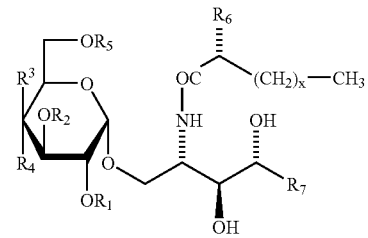

wherein $R_1$, $R_2$ and $R_5$ represent H or a specific monosaccharide; $R_3$ and $R_6$ represent H or OH, respectively; $R_4$ represents H, OH or a specific monosaccharide; X denotes an integer from 1 to 23; $R_7$ represents any one of the following groups (a)-(g): (a) $-(CH_2)_{11}-CH_3$, (b) $-(CH_2)_{12}-CH_3$, (c) $-(CH_2)_{13}-CH_3$, (d) $-(CH_2)_9-CH(CH_3)_2$, (e) $-(CH_2)_{10}-CH(CH_3)_2$, (f) $-(CH_2)_{11}-CH(CH_3)_2$, (g) $-(CH_2)_{11}-CH(CH_3)-C_2H_5$.

A preferred adjuvant of the present invention comprises α-galactosylceramide (α-GalCer), specifically, (2S,3S,4R)-1—O-(α-D-galactopyranosyl)-2-(N-hexacosanoylamino)-1,3,4-octadecanetriol represented by the Formula 2:

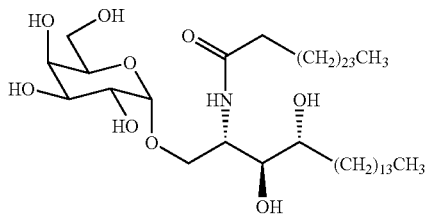

Other examples of glycosylceramides useful in adjuvants of the present invention include, without limitation:

α-glucosylceramide (α-GlcCer), specifically (2S,3S,4R)-1—O-(α-D-glucopyranosyl)-N-hexacosanoyl-2-amino-1,3,4-octadecanetriol, of the Formula 3:

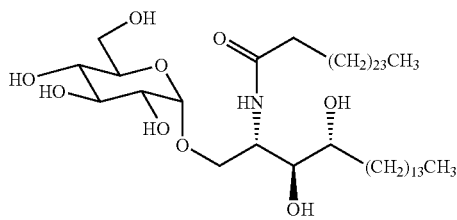

Galα1-6Galα1-1'Cer, specifically (2S,3S,4R)-2-amino-1-O-(α-D-galactopyranosyl-(1-6)-α-D-galactopyranosyl)-N-hexacosanoyl-1,3,4-octadecanetriol, of the Formula 4:

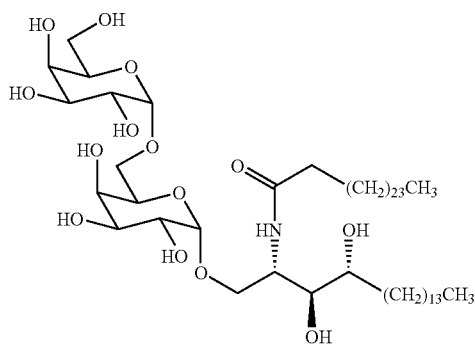

Galα1-6Glcα1-1'Cer, specifically (2S,3S,4R)-2-amino-1-O-(α-D-galactopyranosyl-(1-6)-α-D-glucopyranosyl)-N-hexacosanoyl-1,3,4-octadecanetriol, of the Formula 5:

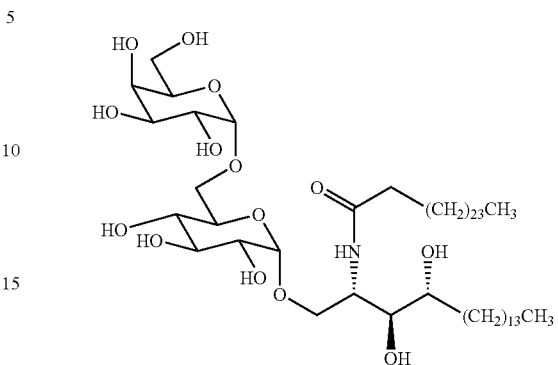

Galα1-2Glcα1-1'Cer, specifically (2S,3S,4R)-2-amino-1-O-(α-D-glucopyranosyl-(1-2)-α-D-galactopyranosyl)-N-[(R)-2-hydroxytetracosanoyl]-1,3,4-octadecanetriol, of the Formula 6:

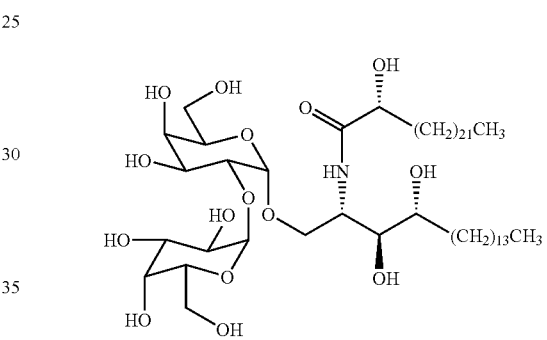

Galβ1-3Galα1-1'Cer, specifically (2S,3S,4R)-2-amino-1-O-(β-D-galactofuranosyl-(1-4)-α-D-galactopyranosyl)-N-[(R)-2-hydroxytetracosanoyl]-1,3,4-octadecanetriol, of the Formula 7:

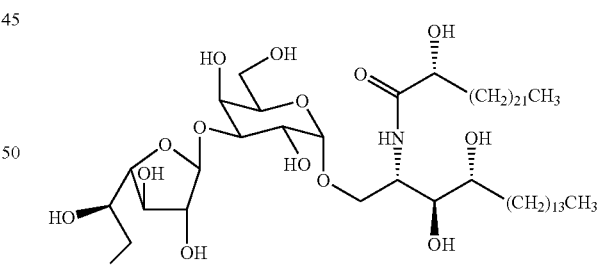

α-GalCer adjuvant component can be either isolated from Okinawan marine sponges (e.g., as described by Natori et al., Tetrahedron, 50: 2771-2784, 1994) or produced synthetically (see, e.g., U.S. Pat. Nos. 5,936,076; 5,780,441; 5,849,716, and 6,071,884; PCT Publication Nos. WO 98/29534, and WO 98/44928; Kobayashi et al., 1995, Oncol. Res., 7:529-534). Similarly, other related glycosylceramide adjuvants of the invention can be either isolated from a natural source (e.g., marine sponges) or produced synthetically (as described in, e.g., U.S. Pat. Nos. 5,936,076; 5,780,441; 5,849,716, and 6,071,884; PCT Publication Nos. WO 98/29534 and WO 98/44928; Morita et al., J. Med. Chem., 38:2176-2187, 1995; Teriyuki et al., J. Med. Chem., 42:1836-1841, 1999).

The antigens used in immunogenic (e.g., vaccine) compositions of the instant invention can be derived from a eukaryotic cell (e.g., tumor, parasite, fungus), bacterial cell, viral particle, or any portion thereof. In the event the material to which the immunogenic response is to be directed is poorly antigenic, it may be additionally conjugated to a carrier molecule such as albumin or hapten, using standard covalent binding techniques, for example, with one of the several commercially available reagent kits.

Examples of preferred antigens of the present invention include (i) malaria-specific antigens such as irradiated plasmodial sporozoites or synthetic peptide antigens comprising at least one T cell and/or B cell epitope of the malarial circumsporozoite (CS) protein (see below); (ii) viral protein or peptide antigens such as those derived from influenza virus (e.g., surface glycoproteins hemagluttinin (HA) and neuraminidase (NA) [such as turkey influenza HA or an avian influenza A/Jalisco/95 H5 HA); immunodeficiency virus (e.g., a feline immunodeficiency virus (FIV) antigen, a simian immunodeficiency virus (SIV) antigen, or a human immunodeficiency virus antigen (HIV) such as gp120, gp160, p18 antigen [described in Example 2, infra]), Gag p17/p24, Tat, Pol, Nef, and Env; herpesvirus (e.g., a glycoprotein, for instance, from feline herpesvirus, equine herpesvirus, bovine herpesvirus, pseudorabies virus, canine herpesvirus, herpes simplex virus (HSV, e.g., HSV tk, gB, gD), Marek's Disease Virus, herpesvirus of turkeys (HVT), or cytomegalovirus (CMV), or Epstein-Barr virus); hepatitis virus (e.g., Hepatitis B surface antigen (HBsAg)); papilloma virus; bovine leukemia virus (e.g., gp51,30 envelope antigen); feline leukemia virus (FeLV) (e.g., FeLV envelope protein, a Newcastle Disease Virus (NDV) antigen, e.g., HN or F); rous associated virus (such as RAV-1 env); infectious bronchitis virus (e.g., matrix and/or preplomer); flavivirus (e.g., a Japanese encephalitis virus (JEV) antigen, a Yellow Fever antigen, or a Dengue virus antigen); Morbillivirus (e.g., a canine distemper virus antigen, a measles antigen, or rinderpest antigen such as HA or F); rabies (e.g., rabies glycoprotein G); parvovirus (e.g., a canine parvovirus antigen); poxvirus (e.g., an ectromelia antigen, a canary poxvirus antigen, or a fowl poxvirus antigen); chicken pox virus (varicella zoster antigen); infectious bursal disease virus (e.g., VP2, VP3, or VP4); Hantaan virus; mumps virus; (iii) bacterial antigens such as lipopolysaccharides isolated from gram-negative bacterial cell walls and staphylococcus-specific, streptococcus-specific, pneumococcus-specific (e.g., PspA [see PCT Publication No. WO 92/14488]), Neisseria gonorrhea-specific Borrelia-specific (e.g., OspA, OspB, OspC antigens of Borrelia associated with Lyme disease such as Borrelia burgdorferi, Borrelia afzelli, and Borrelia garinii [see, e.g., U.S. Pat. No. 5,523,089; PCT Publication Nos. WO 90/04411, WO 91/09870, WO 93/04175, WO 96/06165, W093/08306; PCT/US92/08697; Bergstrom et al., Mol. Microbiol., 3: 479-486, 1989; Johnson et al., Infect. and Immun. 60: 1845-1853, 1992; Johnson et al., Vaccine 13: 1086-1094, 1995; *The Sixth International Conference on Lyme Borreliosis: Progress on the Development of Lyme Disease Vaccine*, Vaccine 13: 133-135, 1995]), and pseudomonas-specific proteins or peptides; (iv) fungal antigens such as those isolated from candida, trichophyton, or ptyrosporum, and (v) tumor-specific proteins such as ErbB receptors, Melan A [MART1], gp100, tyrosinase, TRP-1/gp75, and TRP-2 (in melanoma); MAGE-1 and MAGE-3 (in bladder, head and neck, and non-small cell carcinoma); HPV EG and E7 proteins (in cervical cancer); Mucin [MUC-1] (in breast, pancreas, colon, and prostate cancers); prostate-specific antigen [PSA] (in prostate cancer); carcinoembryonic antigen [CEA] (in colon, breast, and gastrointestinal cancers) and such shared tumor-specific antigens as MAGE-2, MAGE-4, MAGE-6, MAGE-10, MAGE-12, BAGE-1, CAGE-1,2,8, CAGE-3 to 7, LAGE-1, NY-ESO-1/LAGE-2, NA-88, GnTV, and TRP2-INT2.

The foregoing list of antigens are intended as exemplary, as the antigen of interest can be derived from any animal or human pathogen or tumor. With respect to DNA encoding pathogen-derived antigens of interest, attention is directed to, e.g., U.S. Pat. Nos. 4,722,848; 5,174,993; 5,338,683; 5,494,807; 5,503,834; 5,505,941; 5,514,375; 5,529,780; U.K. Patent No. GB 2 269 820 B; and PCT Publication Nos. WO 92/22641; WO 93/03145; WO 94/16716; WO 96/3941; PCT/US94/06652. With respect to antigens derived from tumor viruses, reference is also made to *Molecular Biology of Tumor Viruses, RNA Tumor Viruses*, Second Edition, Edited by Weiss et al., Cold Spring Harbor Laboratory Press, 1982. For a list of additional antigens useful in the compositions of the invention see also Stedman's Medical Dictionary (24th edition, 1982).

In a specific embodiment, the compositions of the present invention provide protective immunity against malaria, in particular against *P. yoelii* and major human plasmodial species *P. falciparum* and *P. vivax*. These compositions comprise one or more of the following components: (i) at least one malaria-specific peptide comprising a T cell epitope capable of eliciting an anti-malarial T-cell response preferably in mammals of diverse genetic backgrounds (e.g., YNRNIVN-RLLGDALNGKPEEK [SEQ ID NO: 1] or SYVPSAEQI [SEQ ID NO: 2] T cell epitope of *P. yoelii* CS protein [Renia et al., J. Immunol., 22: 157-160, 1993; Rodrigues et al., Int. Immunol., 3: 579-585, 1991] or (NVDPNANP)$_n$ [SEQ ID NO: 3] or EYLNKIQNSLSTE WSPCSVT [SEQ ID NO: 4] T cell epitope of *P. falciparum* CS protein [Nardin et al., Science 246:1603, 1989; Moreno et al., Int.Immunol. 3: 997, 1991; Moreno et al., J. Immunol. 151: 489, 1993]); (ii) at least one malaria-specific peptide comprising a B cell epitope (e.g., (NANP)$_3$ [SEQ ID NO: 15] B cell epitope located within the repeat region of the CS protein of *P. falciparum* [Nardin et al., J.Exp.Med. 156: 20, 1982; Nardin et al., Ann. Rev. Immunol. 11: 687, 1993]) capable of stimulating the production of anti-malarial (i.e., neutralizing) antibodies (e.g., directed against the sporozoite stage of the malarial organism). Preferably, the immunogenic compositions of the present invention comprise at least one B cell epitope and at least one T cell epitope. B cell epitopes preferably elicit the production of antibodies that specifically recognize and bind to the malarial circumsporozoite (CS) protein. Alternatively or in addition, the compositions of the invention may comprise B cell and/or T cell epitopes derived from, and reactive with, other malarial components, such as, for example, the *P. vivax* Erythrocyte Secreted Protein-1 or -2 (PvESP-1 or PvESP-2) (see, e.g., U.S. Pat. No. 5,874,527), *P. falciparum* sporozoite surface protein designated Thrombospondin Related Adhesion (Anonymous) protein (TRAP), also called Sporozoite Surface Protein 2 (SSP2), LSA I, hsp70, SALSA, STARP, Hep17, MSA, RAP-1, and RAP-2. In one embodiment, the B cell epitope and T cell epitope components are incorporated into multiple antigen peptides (MAPs), forming a synthetic macromolecular polypeptide containing a high density of the epitopes. Methods for MAP synthesis are well known in the art (see, e.g., Tam, Proc. Natl. Acad. Sci. USA, 85: 5409, 1988; Tam, Meth. Enzymol., 168: 7, 1989).

The present invention also encompasses B cell and T cell epitopes derived from other plasmodial species, including without limitation *P. malariae, P. ovale, P. reichenowi, P.*

*knowlesi, P. cynomolgi, P. brasilianum, P. berghei,* and *P. chabaudi.* These epitopes typically comprise between 8 and 18 amino acid residues, derived from a plasmodial protein.

In another specific embodiment, a preferred antigen of the invention is HIV-specific (such as T cell epitope RGPGRAFVTI [SEQ ID NO: 5] of p18 protein, see Example 2, infra). As disclosed herein, compositions comprising such HIV-specific antigen(s) and an adjuvant comprising glycosylceramide of Formula 1, preferably α-GalCer, are capable of enhancing a T cell response to an HIV antigen in a susceptible mammalian host.

In yet another specific embodiment, an antigen of the invention is influenza A virus-specific. As disclosed herein, co-administation of α-GalCer with a suboptimal dose ($10^5$ p.f.u.) of a recombinant Sindbis virus expressing a CD8+T cell epitope TYQRTRALV (SEQ ID NO: 16) of the nucleoprotein (NP) of the influenza A virus (Tsuji et al., J. Virol., 72:6907-6910, 1998) significantly enhances the CD8+T cell anti-influenza response in a susceptible mammalian host.

To provide additional antigen-derived B and T cell epitopes for use in the compositions of the present invention, these epitopes may be identified by one or a combination of several methods well known in the art, such as, for example, by (i) fragmenting the antigen of interest into overlapping peptides using proteolytic enzymes, followed by testing the ability of individual peptides to bind to an antibody elicited by the full-length antigen or to induce T cell or B cell activation (see, e.g., Janis Kuby, Immunology, pp. 79-80, W. H. Freeman, 1992); (ii) preparing synthetic peptides whose sequences are segments or analogs of a given antigen (see, e.g., Alexander et al., 1994, Immunity, 1:751-61; Hammer et al., 1994, J. Exp. Med., 180:2353-8), or constructs based on such segments, or analogs linked or fused to a carrier or a heterologous antigen and testing the ability of such synthetic peptides to elicit antigen-specific antibodies or T cell activation (e.g., testing their ability to interact with MHC class II molecules both in vitro and in vivo [see, e.g., O'Sullivan et al., 1991, J. Immunol., 147:2663-9; Hill et al., 1991, J. Immunol., 147:189-197]); for determination of T cell epitopes, peptides should be at least 8 to 10 amino acids long to occupy the groove of the MHC class I molecule and at least 13 to 25 amino acids long to occupy the groove of MHC class II molecule, preferably, the peptides should be longer; these peptides should also contain an appropriate anchor motif which will enable them to bind to various class I or class II MHC molecules with high enough affinity and specificity to generate an immune response (see Bocchia et al., Blood 85: 2680-2684, 1995; Englehard, Ann. Rev. Immunol.12: 181, 1994); (iii) sequencing peptides associated with purified MHC molecules (see, e.g., Nelson et al., 1997, PNAS, 94:628-33); (iv) screening a peptide display library for high-affinity binding to MHC class II molecules, TCR, antibodies raised against a full-length antigen, etc. (see, e.g., Hammer et al., 1992, J. Exp. Med., 176:1007-13); (v) computationally analyzing different protein sequences to identify, e.g., hydrophilic stretches (hydrophilic amino acid residues are often located on the surface of the protein and are therefore accessible to the antibodies) and/or high-affinity TCR or MHC class II allele-specific motifs, e.g., by comparing the sequence of the protein of interest with published structures of peptides associated with the MHC molecules (Mallios, Bioinformatics, 15:432-439, 1999; Milik et al., Nat. Biotechnol., 16:753-756, 1998; Brusic et al., Nuc. Acids Res, 26:368-371, 1998; Feller and de la Cruz, Nature, 349:720-721, 1991); (vi) performing an X-ray crystallographic analysis of the native antigen-antibody complex (Janis Kuby, Immunology, p.80, W. H. Freeman, 1992), and (vii) generating monoclonal antibodies to various portions of the antigen of interest, and then ascertaining whether those antibodies attenuate in vitro or in vivo growth of the pathogen or tumor from which the antigen was derived (see U.S. Pat. No. 5,019,384 and references cited therein).

In a specific embodiment, the antigen of the invention may be presented by a recombinant virus expressing said antigen. Preferably, the virus is selected from the group consisting of a recombinant adenovirus, recombinant pox virus, and recombinant Sindbis virus.

In the disclosed compositions, both the antigen and the glycosylceramide adjuvant are present in immunogenically effective amounts. For each specific antigen, the optimal immunogenically effective amount should be determined experimentally (taking into consideration specific characteristics of a given patient and/or type of treatment). Generally, this amount is in the range of 0.1 μg-100 mg of an antigen per kg of the body weight. For the glycosylceramide adjuvant of the present invention, the optimal immunogenically effective amount is preferably in the range of 10-100 μg of the adjuvant per kg of the body weight.

The invention also provides a method for preparing a vaccine composition comprising at least one antigen and an adjuvant comprising glycosylceramide of Formula 1, preferably α-GalCer, said method comprising admixing the adjuvant and the antigen, and optionally one or more physiologically acceptable carriers and/or excipients and/or auxiliary substances.

Formulations and Administration

The invention provides pharmaceutical and vaccine formulations containing therapeutics of the invention (an antigen and glycosylceramide adjuvant either as a single composition or as two separate compositions which can be administered simultaneously or sequentially), which formulations are suitable for administration to elicit an antigen-specific protective immune response for the treatment and prevention of infectious or neoplastic diseases described above. Compositions of the present invention can be formulated in any conventional manner using one or more physiologically acceptable carriers or excipients. Thus, an antigen and/or an adjuvant comprising a glycosylceramide of Formula 1, preferably α-GalCer, can be formulated for administration by transdermal delivery, or by transmucosal administration, including but not limited to, oral, buccal, intranasal, opthalmic, vaginal, rectal, intracerebral, intradermal, intramuscular, intraperitoneal, intravenous, subcutaneous routes, via scarification (scratching through the top layers of skin, e.g., using a bifurcated needle), by inhalation (pulmonary) or insufflation (either through the mouth or the nose), or by administration to antigen presenting cells ex vivo followed by administration of the cells to the subject, or by any other standard route of immunization.

Preferably, the immunogenic formulations of the invention can be delivered parenterally, i.e., by intravenous (i.v.), subcutaneous (s.c.), intraperitoneal (i.p.), intramuscular (i.m.), subdermal (s.d.), or intradermal (i.d.) administration, by direct injection, via, for example, bolus injection, continuous infusion, or gene gun (e.g., to administer a vector vaccine to a subject, such as naked DNA or RNA). Formulations for injection can be presented in unit dosage form, e.g., in ampoules or in multi-dose containers, with an added preservative. The compositions can take such forms as excipients, suspensions, solutions or emulsions in oily or aqueous vehicles, and can contain formulatory agents such as suspending, stabilizing and/or dispersing agents. Alternatively, the active ingredient can be in powder form for reconstitution with a suitable vehicle, e.g., sterile pyrogen-free water, before use.

The present invention also contemplates various mucosal vaccination strategies. While the mucosa can be targeted by local delivery of a vaccine, various strategies have been employed to deliver immunogenic compositions to the mucosa. For example, in a specific embodiment, the immunogenic polypeptide or vector vaccine can be administered in an admixture with, or as a conjugate or chimeric fusion protein with, cholera toxin, such as cholera toxin B or a cholera toxin A/B chimera (see, e.g., Hajishengallis, J Immunol., 154: 4322-32, 1995; Jobling and Holmes, Infect Immun., 60: 4915-24, 1992; Lebens and Holmgren, Dev Biol Stand 82:215-27, 1994). In another embodiment, an admixture with heat labile enterotoxin (LT) can be prepared for mucosal vaccination. Other mucosal immunization strategies include encapsulating the immunogen in microcapsules (see, e.g., U.S. Pat. Nos. 5,075,109; 5,820,883, and 5,853,763) and using an immunopotentiating membranous carrier (see, e.g., PCT Application No. WO 98/0558). Immunogenicity of orally administered immunogens can be enhanced by using red blood cells (rbc) or rbc ghosts (see, e.g., U.S. Pat. No. 5,643,577), or by using blue tongue antigen (see, e.g., U.S. Pat. No. 5,690,938). Systemic administration of a targeted immunogen can also produce mucosal immunization (see, U.S. Pat. No. 5,518,725). Various strategies can be also used to deliver genes for expression in mucosal tissues, such as using chimeric rhinoviruses (see, e.g., U.S. Pat. No. 5,714, 374), adenoviruses, vaccinia viruses, or specific targeting of a nucleic acid (see, e.g., PCT Application No. WO 97/05267).

For oral administration, the formulations of the invention can take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. The compositions of the invention can be also introduced in microspheres or microcapsules, e.g., fabricated from poly-glycolic acid/lactic acid (PGLA) (see, U.S. Pat. Nos. 5,814,344; 5,100,669 and 4,849,222; PCT Publication Nos. WO 95/11010 and WO 93/07861). Liquid preparations for oral administration can take the form of, for example, solutions, syrups, emulsions or suspensions, or they can be presented as a dry product for reconstitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound.

For administration by inhalation, the therapeutics according to the present invention can be conveniently delivered in the form of an aerosol spray presentation from pressurized packs or a nebulizer, with the use of a suitable propellant, e.g., dichlorodifluoro-methane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

Compositions of the present invention can also be formulated in rectal compositions such as suppositories or retention enemas, e.g., containing conventional suppository bases such as cocoa butter or other glycerides.

In addition to the formulations described previously, the compositions can also be formulated as a depot preparation. Such long acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

As disclosed herein, an antigen and/or glycosylceramide adjuvant can be mixed with excipients which are pharmaceutically acceptable and compatible with the active ingredients. Suitable excipients are, for example, water, saline, buffered saline, dextrose, glycerol, ethanol, sterile isotonic aqueous buffer or the like and combinations thereof. In addition, if desired, the preparations may also include minor amounts of auxiliary substances such as wetting or emulsifying agents, pH buffering agents, and/or immune stimulators (e.g., adjuvants in addition to glycosylceramide) that enhance the effectiveness of the pharmaceutical composition or vaccine. Non-limiting examples of additional immune stimulators which may enhance the effectiveness of the compositions of the present invention include immunostimulatory, immunopotentiating, or pro-inflammatory cytokines, lymphokines, or chemokines or nucleic acids encoding them (specific examples include interleukin (IL)-1, IL-2, IL-3, IL-4, IL-12, IL-13, granulocyte-macrophage (GM)-colony stimulating factor (CSF) and other colony stimulating factors, macrophage inflammatory factor, Flt3 ligand, see additional examples of immunostimulatory cytokines in the Section entitled "Definitions"). These additional immunostimulatory molecules can be delivered systemically or locally as proteins or by expression of a vector that codes for expression of the molecule. The techniques described above for delivery of the antigen and glycosylceramide adjuvant can also be employed for the delivery of additional immunostimulatory molecules.

The invention also provides a pharmaceutical pack or kit comprising one or more containers filled with one or more of the ingredients of the immunogenic formulations of the invention. In a related embodiment, the present invention provides a kit for the preparation of a pharmaceutical or vaccine composition comprising at least one antigen and a glycosylceramide-containing adjuvant, said kit comprising the antigen in a first container, and the adjuvant in a second container, and optionally instructions for admixing the antigen and the adjuvant and/or for administration of the composition. Each container of the kit may also optionally include one or more physiologically acceptable carriers and/or excipients and/or auxiliary substances. Associated with such container(s) can be a notice in the form prescribed by a governmental agency regulating the manufacture, use or sale of pharmaceuticals or biological products, which notice reflects approval by the agency of manufacture, use or sale for human administration.

The compositions may, if desired, be presented in a pack or dispenser device which may contain one or more unit dosage forms containing the active ingredient (i.e., an antigen and/or a glycosylceramide-containing adjuvant). The pack may, for example, comprise metal or plastic foil, such as a blister pack. The pack or dispenser device may be accompanied by instructions for administration. Compositions of the invention formulated in a compatible pharmaceutical carrier may also be prepared, placed in an appropriate container, and labeled for treatment of an indicated condition.

Effective Dose and Safety Evaluations

According to the methods of the present invention, the pharmaceutical and vaccine compositions described herein are administered to a patient at immunogenically effective doses, preferably, with minimal toxicity. As recited in the Section entitled "Definitions", "immunogenically effective dose" or "therapeutically effective dose" of disclosed formulations refers to that amount of an antigen and/or glycosylceramide adjuvant that is sufficient to produce an effective immune response in the treated subject and therefore sufficient to result in a healthful benefit to said subject.

Following methodologies which are well-established in the art (see, e.g., reports on evaluation of several vaccine formulations containing novel adjuvants in a collaborative effort between the Center for Biological Evaluation and Food and Drug Administration and the National Institute of Allergy and Infectious Diseases [Goldenthal et al., National Cooperative Vaccine Development Working Group. AIDS Res. Hum. Retroviruses, 1993, 9:545-9]), effective doses and toxicity of the compounds and compositions of the instant invention are first determined in preclinical studies using small animal models (e.g., mice) in which both the antigen and glycosylceramide-containing adjuvant has been found to be immunogenic and that can be reproducibly immunized by the same route proposed for the human clinical trials. Specifically, for any pharmaceutical composition or vaccine used in the methods of the invention, the therapeutically effective dose can be estimated initially from animal models to achieve a circulating plasma concentration range that includes the $IC_{50}$ (i.e., the concentration of the test compound which achieves a half-maximal inhibition of symptoms). Dose-response curves derived from animal systems are then used to determine testing doses for the initial clinical studies in humans. In safety determinations for each composition, the dose and frequency of immunization should meet or exceed those anticipated for use in the clinical trial.

As disclosed herein, the dose of glycosylceramide, antigen(s) and other components in the compositions of the present invention is determined to ensure that the dose administered continuously or intermittently will not exceed a certain amount in consideration of the results in test animals and the individual conditions of a patient. A specific dose naturally varies depending on the dosage procedure, the conditions of a patient or a subject animal such as age, body weight, sex, sensitivity, feed, dosage period, drugs used in combination, seriousness of the disease. The appropriate dose and dosage times under certain conditions can be determined by the test based on the above-described indices and should be decided according to the judgment of the practitioner and each patient's circumstances according to standard clinical techniques. In this connection, the dose of an antigen is generally in the range of 0.1 μg-100 mg per kg of the body weight, and the dose of the glycosylceramide adjuvant required for augmenting the immune response to the antigen is generally in the range of 10-100 μg per kg of the body weight.

Toxicity and therapeutic efficacy of glycosylceramide-containing immunogenic compositions of the invention can be determined by standard pharmaceutical procedures in experimental animals, e.g., by determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_5/ED_{50}$. Compositions that exhibit large therapeutic indices are preferred. While therapeutics that exhibit toxic side effects can be used (e.g., when treating severe forms of cancer or life-threatening infections), care should be taken to design a delivery system that targets such immunogenic compositions to the specific site (e.g., lymphoid tissue mediating an immune response, tumor or an organ supporting replication of the infectious agent) in order to minimize potential damage to other tissues and organs and, thereby, reduce side effects. As disclosed herein (see also Background Section and Examples), the glycosylceramide adjuvant of the invention is not only highly immunostimulating at relatively low doses (e.g., 10-100 μg of the adjuvant per kg of the body weight) but also possesses low toxicity and does not produce significant side effects.

As specified above, the data obtained from the animal studies can be used in formulating a range of dosage for use in humans. The therapeutically effective dosage of glycosylceramide-containing compositions of the present invention in humans lies preferably within a range of circulating concentrations that include the $ED_{50}$ with little or no toxicity. The dosage can vary within this range depending upon the dosage form employed and the route of administration utilized. Ideally, a single dose should be used.

EXAMPLES

The following Example illustrates the invention without limiting its scope.

Example 1

The Natural Killer T Cell Ligand
α-Galactosylceramide Enhances and Prolongs the Duration of Protective Immunity Induced by Malaria Vaccines Methods Parasites and Their Use for Immunization and Challenge.

*P. yoelii* (17X NL strain) sporozoites were obtained by dissecting the mosquito salivary glands as described (Rodrigues et al., Int. Immunol., 3: 579-585, 1991; Gonzalez-Aseguinolaza et al., Proc. Natl. Acad. Sci. USA, 97: 8461-8466, 2000). For immunization, sporozoites were radiation-attenuated by exposing them to 12,000 rad, and then injected intravenously into the tail vein or subcutaneously into the base of the tail of the mice. $1 \times 10^4$ and $1 \times 10^5$ γ-spz were used to immunize mice for protection assay and an ELISPOT assay, respectively. Parasitemia was determined by microscopic examination of Giemsa stained thin blood smears obtained daily from day 3 to day 14 post-sporozoite inoculation. Complete protection was defined as the absence of parasitemia during this entire period.

Immunization with Recombinant Viruses.

A sub-optimal dose ($1 \times 10^7$ p.f.u.) of recombinant adenovirus expressing the entire *P. yoelii* CS protein, AdPyCS (Rodrigues et al., J. Immunol., 158: 1268-1274, 1997), was used to immunize mice. The recombinant Sindbis virus expressing the CD8+T cell epitope (SYVPSAEQI [SEQ ID NO: 2]) of *P. yoelii* CS protein, SIN(Mal), and the recombinant Sinbis virus expressing the CD8+T cell epitope (RGPGRAFVTI

[SEQ ID NO: 5]) of HIV p18 protein, SIN(P18), were constructed as described (Tsuji et al., J. Virol., 72: 6907-6910, 1998; Villacres et al., Virology, 270: 54-64, 2000), and $1\times10^5$ p.f.u. of the viruses were inoculated s.c., as a sub-optimal dose.

Mice.

BALB/c and B10.D2 mice were purchased from The Jackson Laboratory (Bar Harbor, Me.) and maintained under standard conditions in the Animal Facility. Vα14 NKT-deficient mice (Jα281$^{-/-}$) were established by specific deletion of the Jα281 gene segment with homologous recombination and aggregation chimera techniques (Cui et al., Science, 278: 1623-1626, 1997; Gonzalez-Aseguinolaza et al., Proc. Natl. Acad. Sci. USA, 97: 8461-8466, 2000) and used after 3-4 backcrosses to BALB/c mice. CD1d-deficient mice (CD1d$^{-/-}$) were generated from embryonic stem cells of 129 origin and used after 7-8 backcrosses to BALB/c (Mendiratta et al., Immunity, 6: 469-477,1997; Gonzalez-Aseguinolaza et al., Proc. Natl. Acad. Sci. USA, 97: 8461-8466,2000). IFN-γ receptor-deficient mice (IFNγ R$^{-/-}$) were obtained from Swiss Institute for Experimental Cancer Research (Epalinges, Switzerland), and used after 3 backcrosses to B10.D2 (Rodrigues et al., Parasite Immunol., 22: 157-160, 2000). Mice of either sex were used at 6-8 weeks.

α-GalCer.

α-GalCer, [(2S,3S,4R)-1—O-(α-D-galactopyranosyl)-2-(N-hexacosanoylamino)-1,3,4-octadecanetriol], was synthesized by Kirin Brewery (Gunma, Japan) using the method disclosed (Morita et al., J. Med. Chem., 38:2176-2187, 1995; Teriyuki et al., J. Med. Chem., 42:1836-1841, 1999). The original product was dissolved in 0.5% polysorbate-20 (Nikko Chemical, Tokyo) in 0.9% NaCl solution and diluted with PBS just before use.

Peptide Immunization and α-GalCer Treatment.

Mice were immunized with peptides corresponding to the CD4+ T cell epitope (YNRNIVNRLLGDALNGKPEEK [SEQ ID NO: 1]) (Renia et al., J. Immunol., 22: 157-160, 1993) or the CD8+ T cell epitope (SYVPSAEQI [SEQ ID NO: 2]) (Rodrigues et al., Int. Immunol., 3: 579-585, 1991) of the P. yoelii CS protein. The peptide representing the CD8+ epitope of the CS protein was emulsified in incomplete Freund's adjuvant (IFA), while the peptide containing the CS-specific CD4+ epitope was emulsified in complete Freund's adjuvant (CFA). Mice were subcutaneously immunized with 10 mg of the peptide. Some of the immunized mice were injected intraperitoneally with α-GalCer, and others with vehicle alone as a control. The dose and time of administration are indicated below.

Quantification of Epitope-Specific CD4+ and CD8+ T Cells by an ELISPOT Assay.

An ELISPOT assay was performed to determine the number of CS-specific CD4+ and CD8+ T cells, producing IFN-γ or IL-4 (Miyahira et al., J. Immunol. Methods, 181: 45-54, 1995). Briefly, 96 well nitrocellulose plates (Millipore, Bedford, Mass.) were coated with anti-mouse IFN-γ monoclonal antibodies (mAb), or anti-mouse IL-4 mAb. After overnight incubation at room temperature, the wells were washed repeatedly and blocked with culture medium for 1 hour at 37° C. The MHC-compatible target cells, A20.2J B cell lymphoma, expressing both MHC class I and II H-2$^d$ molecules, were incubated for 1 hour at 37° C. with the synthetic peptide representing the CD4+ T cell epitope (YNRNIVNR-LLGDALNGKPEEK [SEQ ID NO: 1]) or CD8+ T cell epitope (SYVPSAEQI [SEQ ID NO: 2]) of the P. yoelii CS protein, or CD8+ T cell epitope (RGPGRAFVTI [SEQ ID NO: 5]) of the HIV p18 protein. After irradiating the peptide-pulsed target cells, the cells were added to the ELISPOT wells. Untreated target cells were used as negative controls. Serially diluted lymphocytes isolated from the spleen or lymph nodes of immunized mice were co-cultured with $1.5\times10^5$ target cells in the ELISPOT wells. After incubating the plates 24 h for IFN-γ detection or 48 h for IL-4 detection at 37° C. and 5% $CO_2$, the plates were treated as previously described (Rodrigues et al., J. Immunol., 158: 1268-1274, 1997), and the number of spots corresponding to IFN-γ and IL-4 secreting cells determined.

Quantification of P. yoelii rRNA in the Liver of Sporozoite-Inoculated Mice by Real-Time PCR.

Quantification of P. yoelii rRNA was performed as described (Bruna-Romero et al., Int. J. Parasitol. 31: 1499-1502, 2001). Briefly, total RNA was isolated by the method of Chomczynski and Sacchi (Chomczynski and Sacchi, Anal. Biochem., 162: 156-159, 1987) from the liver of mice sacrificed 42 hours after injection with $1\times10^4$ P. yoelii sporozoites. After reverse transcription of the extracted RNA, cDNA was generated and its amount analyzed by real-time PCR, using the ABI Prism 5700 Sequence Detection system(PE Biosystems, Foster City, Calif.; Bruna-Romero et al., Int. J. Parasitol., 31: 1499-1502, 2001). Primers and fluorogenic probe with the following sequences were custom designed using the ABI Prism primer Express software (PE Biosystems, Foster City, Calif.), using P. yoelii (17XNL) 18S rRNA sequence (Bruna-Romero et al., Int. J. Parasitol., 31: 1499-1502, 2001). The primers, 5'-GGGGATTGGT TTTGACGTTTTTGCG-3' (forward primer; SEQ ID NO: 17), and 5'-AAGCAT-TAAATAAAG CGAATACATCCTTAT-3' (reverse primer; SEQ ID NO: 18), were obtained from Operon Technologies Inc. (Alameda, Calif.). The specific fluorogenic probe, PyNYU, 5'-FAM-CAATTG GTTTACCTTTTGCTCTTT-TAMRA-3' (SEQ ID NO: 19), was obtained from PE Applied biosystems (Foster City, Calif.), and was generated with 5-propyne-2'-deoxyuridine (turbo Taqman probe) to achieve a proper Tm. The reaction mix contained 5 μl of 10× Taqman buffer A (PE Biosystems, Foster City, Calif.), 3.5 mM $MgCl_2$, 200 μM dNTP, 0.3 μM forward primer, 0.3 μM reverse primer, 50 nM turbo Taqman probe PyNYU, 1.25 U AmpliTaq Gold DNA polymerase, and water up to 50 μl final reaction volume. The temperature profile included 95° C. for 10 minutes and 35 cycles of denaturation at 95° C. for 15 seconds and annealing/extension at 60° C. for 1 minute. The PCR products were visualized in 2% agarose-1×TAE (50 mM Tris-acetate, pH 8.0, 1 mM EDTA) gels stained with 0.5 mg/ml ethidium bromide. Digital images from the gels were obtained using the Gel Doc 2000 gel documentation system (BioRad, Hercules, Calif.), and analyzed by densitometry using Quantity One software (BioRad, Hercules, Calif.). The precise amount of parasite-derived 18S cDNA molecules detected in this assay was determined by linear regression analysis using CT values obtained from both liver samples and those obtained from a standard curve generated with known amounts of plasmid 18S cDNA.

Quantification of α-GalCer-Specific Cells by ELISPOT Assay.

The relative numbers of IFN-γ and/or IL-4 producing α-GalCer-specific lymphocytes were determined using an ELISPOT assay. Lymphocytes were isolated from the liver of wild-type and IFN-γ R-deficient mice, as described (Rodrigues et al., J. Immunol., 158: 1268-1274, 1997). After 12 hour incubation with 100 ng/ml of α-GalCer or vehicle at a cell density of $10^7$ cells/ml, serially diluted lymphocytes, starting at $1\times10^6$ cells per well, were placed into ELISPOT wells coated with corresponding anti-cytokine antibodies. After incubating the plates for 24 hours at 37° C. and 5% $CO_2$, the plates were developed as described (Rodrigues et al., J. Immunol., 158: 1268-1274, 1997).

Flow Cytometric Analysis Using CD1d/α-GalCer Tetramers.

α-GalCer-specific lymphocytes were identified using CD1d/α-GalCer tetrameric complexes, consisting of CD1d molecules and α-GalCer, as previously described (Matsuda et al., J. Exp. Med., 192: 741-754, 2000). Freshly isolated hepatic lymphocytes were incubated first with phycoerythrin (PE)-labelled tetrameric complexes, followed by a second incubation with FITC-labelled anti-CD3 monoclonal antibody. The cells were then analyzed by a FACScalibur instrument (Becton Dickinson, San Jose, Calif.) using CELLQUEST software (Becton Dickinson).

Indirect Immunoflurescence Assay (IFA).

Sera of immunized mice were obtained just before their challenge with sporozoites, and their Ab titers were measured using P. yoelii sporozoites in an indirect immunofluorescence assay (IFA). In brief, P. yoelii sporozoites were placed on multispot glass slides, and air-dried. After 1 hour of incubation with the sera, diluted in PBS containing 1% BSA, the slides were washed with PBS and incubated 1 hour with FITC- labelled affinity purified goat anti-mouse Ab (Kirkegaard & Perry Laboratories, Gaithersburg, Md.). The slides were then washed and mounted in PBS containing 50% (v/v) glycerol and 1% (w/v) Evans blue to reduce bleaching. The highest serum dilution resulting in fluorescence of the sporozoites was considered to be the IFA titer.

Measurement of Ab Isotype Level by ELISA.

Sera of immunized mice were obtained prior to their challenge with sporozoites, and the levels of CS-specific IgM, IgG1, IgG2a, and IgE isotypes were measured using the Mouse Hybridoma Subtyping Kit (Boehringer Mannheim, Mannheim, Germany). Briefly, plates were coated with 10 mg/ml of B cell epitope $(QGPGAP)_2$ (Charoenvit et al., J. Immunol., 146: 1020-1025, 1991) of the P. yoelii CS protein, blocked with PBS containing 1% BSA, and incubated for 1 hour with 1:5 dilution of sera from immunized and non-immunized mice. The plates were then washed and anti-mouse IgM, IgG1a, IgG2a (Boehringer Mannheim) and IgE (Southern Biotechnology Associates, Inc., Birmingham, Ala.) conjugated to peroxidase were added, followed by incubation with the substratre 2,2-Azino-di-[3-ethylbenzthiazoline sulfonate (6)], according the manufacture's instruction.

Statistical Analysis.

Student's t test was used for all comparisons. Only P values below 0.01 were considered significant. Data are presented as mean values±SD.

Results

α-GalCer Enhances Protective Anti-Malaria Immunity

To assess the ability of α-GalCer to enhance the protective anti-malaria immune response induced by immunization with a suboptimal dose of irradiated sporozoites, BALB/c mice were immunized intravenously with a sub-optimal dose ($1\times10^4$) of irradiated sporozoites (γ-spz) together with different doses of γ-GalCer (0.5, 1, 2 μg). Two weeks later, these different groups of mice were challenged with $1\times10^4$ live P. yoelii sporozoites, and the levels of protective anti-malaria immunity were measured by determining the amount of parasite-specific rRNA in the liver using a highly sensitive real-time PCR assay (Bruna Romero et al., Int. J. Parasitol. 31: 1499 1502, 2001). α-GalCer administration significantly enhanced, in a dose-dependent manner, the level of protective immunity (% inhibition of the liver stage development) elicited by immunization with γ-spz (FIG. 1A). Indeed, the parasite load in the livers of γ-spz-immunized mice administered with 2 μg of α-GalCer was 10 times smaller than that in the livers of mice immunized with γ-spz alone.

The present inventors also determined the titers of anti-sporozoite antibodies using an immunofluorescence assay (IFA) of air-dried P. yoelii sporozoites, as well as the titers of antibody against the circumsporozoite (CS) protein, the major surface antigen of sporozoites, using ELISA. The antibody titers were identical among the groups of γ-spz-immunized mice regardless of whether or not they received α-GalCer (FIG. 1A). When the immunoglobulin isotype of the anti-CS antibodies was determined, no significant differences in IgE, $IgG_1$, $IgG_{2a}$ or IgM isotype profiles of anti-CS antibodies were detected between α-GalCer-treated and untreated mice. These results indicate that anti-malarial humoral response is not affected by α-GalCer treatment.

Figure 1B:
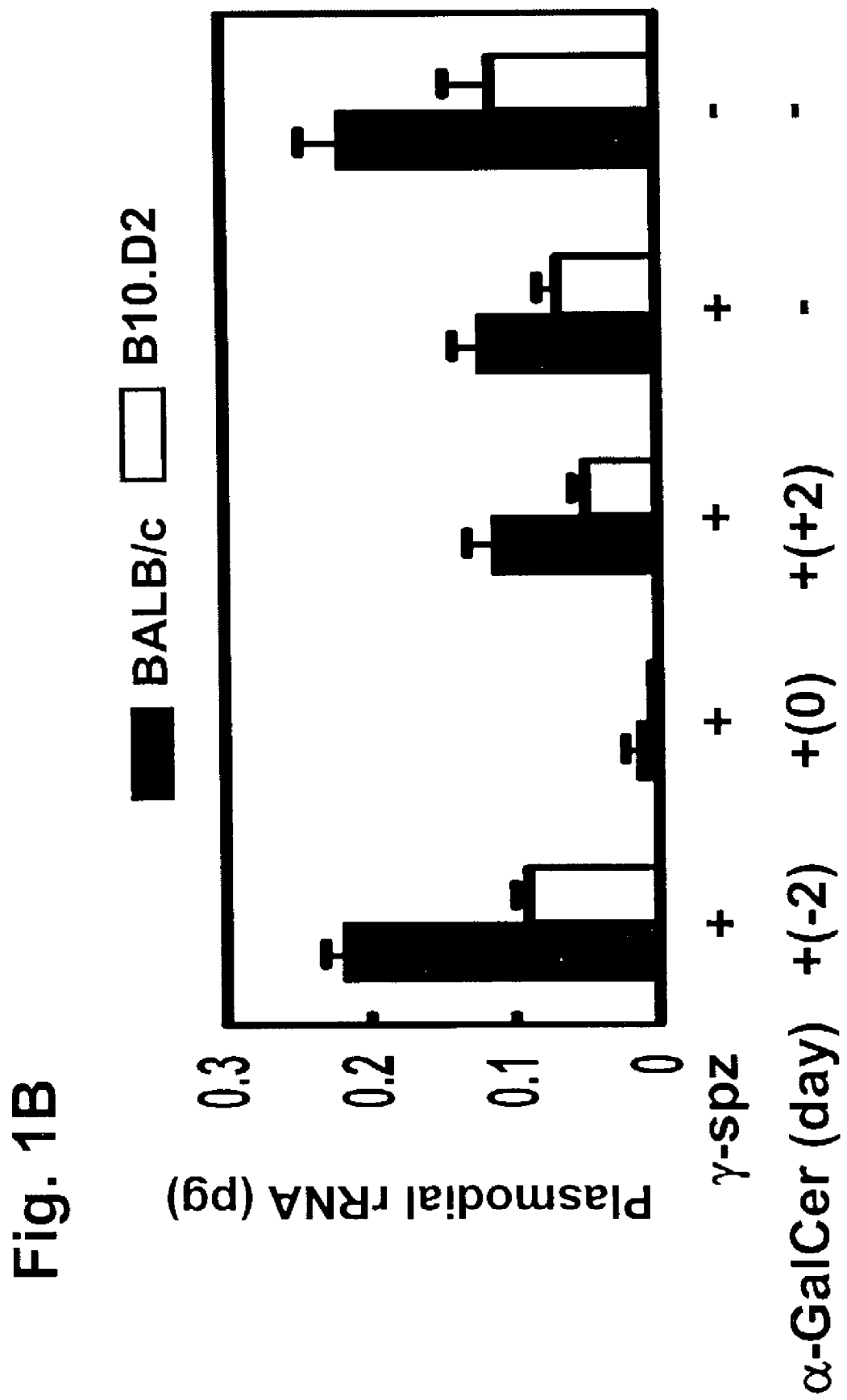

The kinetics of the adjuvant activity displayed by α-GalCer were then examined by administering 2 μg of the glycolipid to BALB/c mice on the same day, two days before or two days after intravenous immunization with $1\times10^4$ γ-spz. The highest level of protective anti-malaria immunity was elicited when α-GalCer was administered on the same day as γ-spz (FIG. 1B). The administration of α-GalCer two days after γ-spz immunization did not significantly enhance the level of protective immunity induced by sporozoites alone. Interestingly, when α-GalCer was administered two days prior to γ-spz immunization, protective immunity was completely abolished. It is possible that α-GalCer administered two days earlier might have eliminated the sporozoites before they could be processed and presented by antigen presenting cells, thereby preventing the induction of a malaria-specific immune response. As shown in the previous study by the present inventors (Gonzalez-Aseguinolaza et al., Proc. Natl. Acad. Sci. USA, 97: 8461-8466, 2000), α-GalCer administered two days prior to challenge with live sporozoites completely eliminates the parasites from the liver in a manner dependent on NKT cells and IFN-γ. Similar kinetics of the adjuvant activity of α-GalCer were observed in B10.D2 mice. (FIG. 1B).

Figure 1C:
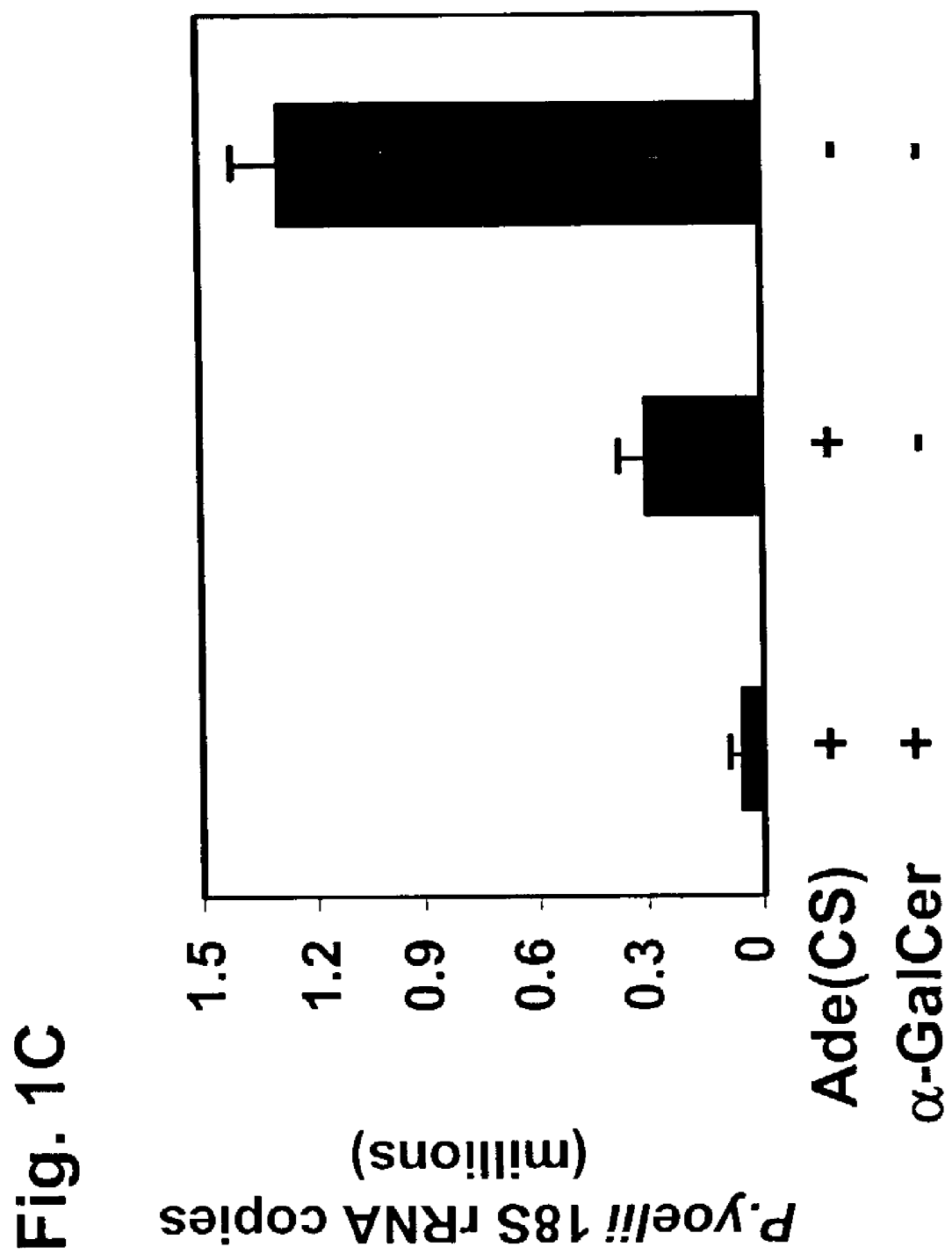
Figure 1D:
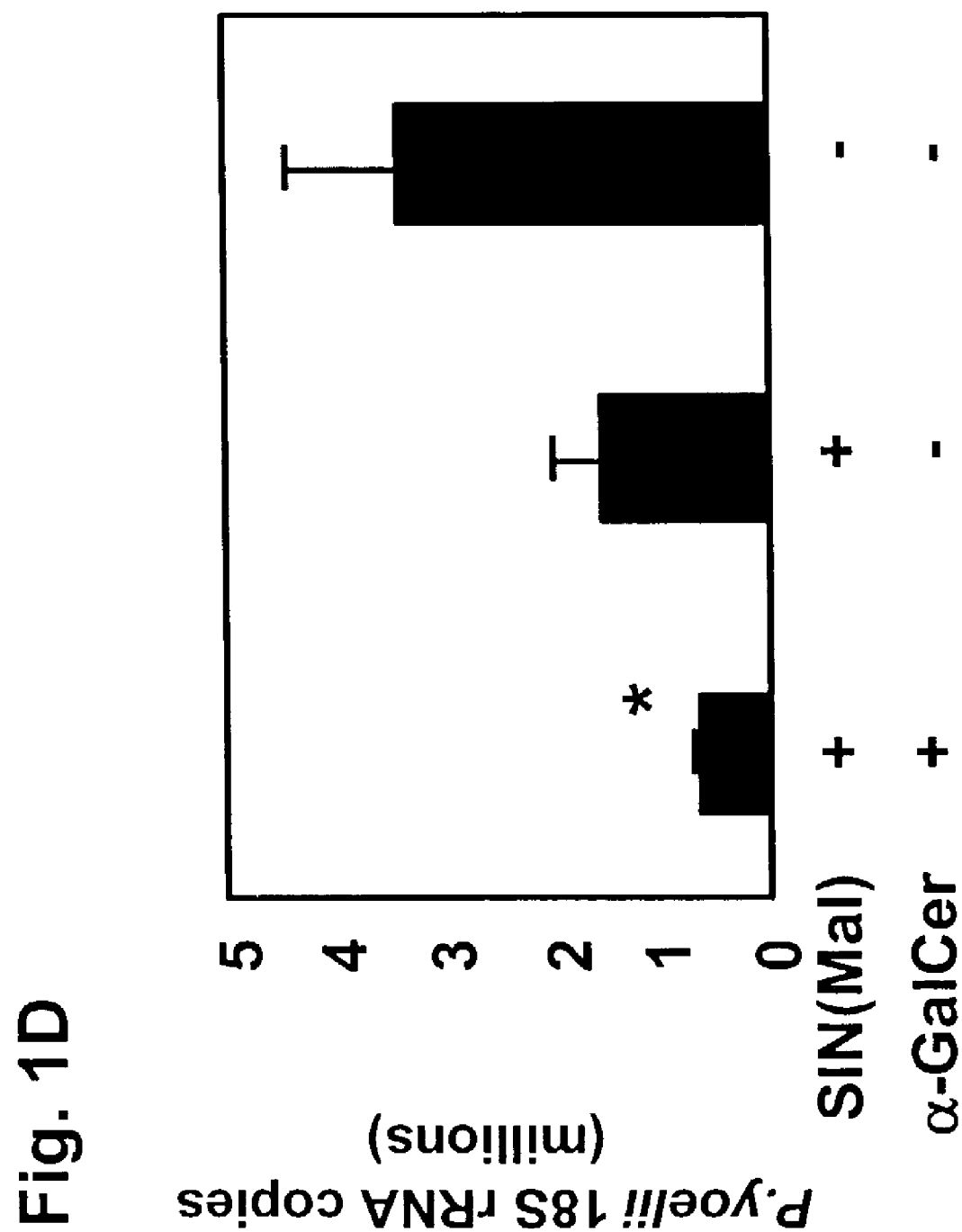

Co-Administration of α-GalCer with a Malaria Antigen Enhances Malaria-Specific T Cell Responses, Particulary Those of CD8+T Cells To determine whether α-GalCer-mediated enhancement of the protective immune response against malaria is a particular phenomenon related to γ-spz immunization, or a more general phenomenon independent of the immunogen administered, α-GalCer was administered to BALB/c mice on the same day as subcutaneous immunization with a sub-optimal dose of recombinant adenovirus expressing the whole CS protein, AdPyCS (Rodrigues et al., J. Immunol., 158: 1268-1274,1997), or recombinant Sindbis virus expressing the CD8+ T cell epitope of the CS protein, SIN(Mal) (Tsuji et al., J. Virol. 72: 6907-6910, 1998). As shown in FIGS. 1C and 1D, α-GalCer significantly enhances the protective immune response induced by immunization with a sub-optimal dose of the two different recombinant viruses. In the case of AdPyCS, the protection was augmented almost 10 times to that of control, and in the case of SIN(Mal), the protection after co-administration with α-GalCer was enhanced 3 times.

To further assess the adjuvant activity of α-GalCer co-administered with vaccines, parasitemia (i.e., the presence of parasites in the blood) was monitored daily by microscopic examination of thin blood smears. Briefly, BALB/c mice were immunized either intravenously with $1×10^4$ γ-spz or subcutaneously with $1×10^7$ p.f.u. of AdPyCS, doses which otherwise fail to confer protection against malaria, with or without α-GalCer treatment. Two weeks later, all mice were challenged with 50 viable *P. yoelii* sporozoites, and determined the occurrence of blood infection by monitoring parasitemia. 28 out of 30 α-GalCer-treated, γ-spz-immunized mice were protected, while most of the α-GalCer-untreated, γ-spz-immunized mice developed malaria infection (Table I). Similarly, administration of α-GalCer together with AdPyCS strongly enhanced the protective effect induced by a sub-optimal dose of the virus. On the other hand, administration of α-GalCer alone failed to protect the challenged mice. Overall, these results corroborate the liver stage data (FIG. 1), and together indicate that α-GalCer administration increases the efficacy of a sub-optimal immunizing dose of both γ-spz and recombinant viruses, revealing a profound adjuvant effect.

TABLE I

α-GalCer Enhances Protective Immunity Induced by Malaria Immunogens

| Immunogen | Number of mice protected/number challenged | % protection (no parasitemia) |
| --- | --- | --- |
| γ-spz* | 6/30 | 20 |
| γ-spz + α-GalCer | 28/30 | 93 |
| AdPyCS* | 2/30 | 7 |
| AdPyCS + α-GalCer | 24/30 | 80 |
| α-GalCer | 0/30 | 0 |
| None | 0/30 | 0 |

*BALB/c mice were immunized either intravenously with $1 × 10^4$ γ-spz or subcutaneously with $1 × 10^7$ p.f.u. of AdPyCS.

α-GalCer Enhances T Cell Responses Elicited by Various Vaccines

In order to determine which components of the malaria-specific T cell responses (i.e., CD4+ and/or CD8+ T cell responses) are enhanced by co-injection of α-GalCer with γ-spz, these immune parameters were compared in γ-spz-immunized mice treated with or without α-GalCer. For this purpose, BALB/c mice were immunized with $1×10^5$ γ-spz, either together with a vehicle (0.5% polysorbate-20, Nikko Chemical, Tokyo) or α-GalCer. Two or six weeks later, splenic lymphocytes were isolated, and the numbers of CS-specific, IFN-γ- and IL-4-secreting CD8+ and CD4+T cells were determined by an ELISPOT assay (Rodrigues et al., J. Immunol., 158: 1268-1274, 1997). As shown in FIG. 2A, α-GalCer treatment strikingly enhanced the level of CS-specific T cell responses elicited by γ-spz at two weeks after immunization. Specifically, α-GalCer increased the number of IFN-γ-secreting CS-specific CD8+ T cells approximately seven fold compared to those induced by γ-spz immunization alone (FIG. 2A). Furthermore, the number of IFN-γ-secreting CS-specific CD4+ T cells was also significantly increased, albeit to a lesser degree (FIG. 2A). More importantly, the administration of α-GalCer not only enhanced the level of CS-specific CD8+ T cell response but also prolonged the duration of the response (FIG. 2A; see below). Such strong enhancement of the T cell responses by α-GalCer treatment was not observed when α-GalCer was administered two days prior to or two days after the γ-spz immunization. No difference was found in the numbers of CS-specific CD4+ or CD8+ T cells secreting IL-4, indicating that α-GalCer treatment primarily enhances antigen-specific Th1-type responses in the present experimental system. Because similar results were obtained in both BALB/c and B10.D2 mice, it can be concluded that the adjuvant effect of α-GalCer is not influenced by the different genetic backgrounds of these mice.

Since it was found that α-GalCer administration strongly augments the level of CS-specific T cell responses in sporozoite-immunized mice, the present inventors have decided to determine whether α-GalCer could also enhance CS-specific T cell responses upon peptide immunization as well as upon immunization with recombinant viruses. α-GalCer was administered to BALB/c mice at the same time as subcutaneous immunization with (i) 10 mg of a synthetic peptide corresponding to either the CD8+ T cell epitope or the CD4+ T cell epitope of the CS protein or (ii) suboptimal dose of AdPyCS. Ten days later, lymph node cells (for peptide immunization) and splenocytes (for viral immunization) were obtained from these groups of mice, and the numbers of CS-specific T cells secreting IFN-γ or IL-4 were determined by an ELISPOT assay. The number of both CS-specific CD4+ and CD8+ T cells secreting IFN-γ elicited in α-GalCer-treated, peptide-immunized mice was significantly higher than the number of such T cells in peptide-immunized mice without α-GalCer treatment. α-GalCer administered two days before or two days after the peptide immunization was also able to significantly enhance the CS-specific T cell responses, albeit to a lesser degree than the responses enhanced by simultaneous administration of α-GalCer with the peptides. The number of both CS-specific CD4+ and CD8+ T cells secreting IFN-γ elicited in α-GalCer-treated AdPyCS-immunized mice was more than 10-fold higher than that of T cells from a group of mice immunized with the virus alone (FIG. 2B). When SIN(Mal) was used, it was found that α-GalCer treatment also increases the number of CS-specific CD8+ T cells secreting IFN-γ (FIG. 2C).

The present inventors have also examined whether the adjuvant activity of α-GalCer is a phenomenon related specifically to the H-2Kd-restricted CD8+ T cell epitope of the CS, or can be applied to non-malarial epitopes. For this purpose BALB/c mice were immunized with a recombinant Sindbis virus expressing a H-2Dd-restricted CD8+ T cell epitope (RGPGRAFVTI [SEQ ID NO: 5]) of p18 protein (V3 loop) of HIV (Villacres et al., Virology, 270: 54-64, 2000). α-GalCer co-administration increased the number of p18-specific IFN-γ-secreting CD8+ T cells induced by immunization with SIN(p18) 4-fold (FIG. 2C). These results indicate that (i) α-GalCer treatment enhances a CD8+ T cell response specific for HIV antigen in mice, and that (2) α-GalCer treatment enhances a CD8+ T cell response induced by a recombinant Sindbis virus expressing a foreign epitope, i. e., another form of antigen presentation. More generally, the data presented herein demonstrate that the enhancement of the cellular immune response by treatment with α-GalCer is independent of the antigen delivery system (attenuated pathogen, peptide or recombinant virus) and the epitope.

α-GalCer Prolongs the Duration of Both Malaria-Specific T Cell Responses and Anti-Malaria Protection Elicited by Sporozoite Immunization Next, the duration of the CS-specific CD8+ T cell responses was compared in α-GalCer-treated, sporozoite-immunized mice, and in sporozoite-immunized mice without α-GalCer treatment. BALB/c mice were immunized with $1×10^5$ γ-spz, with or without α-GalCer-treatment, and two or four weeks later, splenocytes were obtained from these mice and the number of CS-specific CD8+ T cells secreting IFN-γ determined by an ELISPOT assay. The administration of α-GalCer not only enhanced the level of the CS-specific CD8+ T cell response, but also prolonged the duration of this response (FIG. 3A).

To determine the adjuvant effect of α-GalCer on the duration of protection against malaria, parasitemia (i.e., the presence of the parasites in the blood) was monitored daily via microscopic inspection of thin blood smears in two separate experiments. In experiment 1, two groups of mice, one treated with α-GalCer and the other untreated, were immunized with $1 \times 10^4$ γ-spz, a dose that fails to confer protection against malaria 2 weeks after immunization. Two weeks later, all mice were challenged with 50 viable P. yoelii sporozoites, and the occurrence of blood infection was determined by monitoring parasitemia. In experiment 2, two groups of mice, one treated with α-GalCer and the other untreated, were immunized with $1 \times 10^5$ γ-spz, a dose that induces complete protection 2 weeks after immunization but not 4 weeks after. Four weeks later, these immunized mice, as well as naive controls were challenged with 50 live sporozoites, and the course of infection was determined as described above. It was found that nine out of ten α-GalCer-treated, sporozoite-immunized mice were protected in both experiments, while most of the sporozoite-immunized mice that did not receive α-GalCer-treatment developed malaria infection (FIG. 3B). These results corroborate data obtained in studies determining the parasite burden in the liver by RT-PCR, and further demonstrate that α-GalCer administration prolongs the duration of a protective immune response and increases the efficacy of a sub-optimal immunizing dose of irradiated sporozoites, revealing an adjuvant effect.

The Activity of α-GalCer Requires CD1D Molecules, Vα14 NKT Cells and IFN-γ

As α-GalCer has been shown to activate NKT cells in the context of CD1d molecules (see the references from the Background Section, e.g., Kawano et al., Science, 278: 1626-1629, 1997), cellular mechanism underlying α-GalCer's adjuvant activity was investigated using mice lacking CD1d molecules as well as mice deficient in T cells expressing the canonical NKT cell receptor. Briefly, these knockout mice, along with wild-type controls, were immunized with a sub-optimal dose of γ-spz ($1 \times 10^4$) together with or without α-GalCer treatment. Two weeks later, these immunized mice, as well as non-immunized controls were challenged with live sporozoites, and the adjuvant levels of protective anti-malaria immunity were determined. As shown in FIG. 4A, the administration of α-GalCer, which increased the level of γ-spz-induced protective immunity in wild-type mice, failed to enhance the protective immunity in CD1d-deficient mice, as well as in Jα281-deficient mice, which lack Vα14 NKT cells. These results indicate that the adjuvant activity of α-GalCer is dependent on both CD1d molecules and Vα14 NKT cells.

To further demonstrate the importance of CD1d molecules and Vα14 NKT cells for the adjuvant activity of α-GalCer, the number of CS-specific CD8+ T cells was measured in γ-spz-immunized, α-GalCer-treated or untreated mice, deficient in either CD1d or Vα14 NKT cells. As shown in FIG. 4B, α-GalCer treatment failed to increase the number of CS-specific CD8+ T cells induced by γ-spz immunization in CD1d-deficient mice compared to that of untreated mice, indicating that α-GalCer requires CD1d to enhance the CS-specific CD8+ T cell response. Interestingly, in γ-spz-immunized and α-GalCer-treated, Jα281-deficient mice, the number of CS-specific CD8+ T cells was significantly increased compared to that of untreated mice (FIG. 4B). However, this increase did not reach the level of α-GalCer-treated, γ-spz-immunized wild-type mice (FIG. 4B) and did not enhance the level of protective anti-malaria immunity (FIG. 4A). These findings, therefore, demonstrate the importance of Vα14 NKT cells in mediating the adjuvant effect of α-GalCer.

Lastly, in order to gain insight into the molecular mechanism underlying α-GalCer's adjuvant activity, mice lacking the IFN-γ receptor (IFN-γ R$^{-/-}$) were immunized with γ-spz with or without α-GalCer co-treatment, and ten days later, the numbers of CS-specific IFN-γ-secreting CD8+ and CD4+ T cells were analyzed using an ELISPOT assay. α-GalCer co-administration failed to augment the number of CS-specific IFN-γ-secreting CD8+ and CD4+ T cells in the γ-spz-immunized knockout mice (FIG. 5A). It has been reported that mice deficient in different molecules such as GM-CSF receptor β-chain (Sato et al., Proc. Natl. Acad. Sci. USA, 96: 7439-7444, 1999) and Fas (Mieza et al., J. Immunol., 156: 4035-4040, 1996) are also partially deficient in NKT cells. To exclude the possibility that the absence of the IFN-γ receptor results in a decreased number and/or defective function of NKT cells, the presence and the function of NKT cells in these IFN-γR$^{-/-}$ mice was analyzed by CD1d/α-GalCer tetramer staining and ELISPOT assay. Flow cytometric analysis using CD1d/α-GalCer tetramers revealed that the percentage of α-GalCer-specific NKT cells among hepatic lymphocytes in IFN-γR$^{-/-}$ mice is similar to that in wild-type mice (FIG. 5B). In addition, the number of α-GalCer specific cells secreting IFN-γ in the liver (FIG. 5C) and spleen of wild-type and IFN-γR$^{-/-}$ mice is similar, eliminating the possibility that the lack of adjuvant activity was due to a defect in the NKT cell population. Collectively, these results indicate that α-GalCer's adjuvant activity is dependent on IFN-γ production.

Discussion

The present Example addresses the ability of the NKT cell ligand, α-GalCer, to act as an adjuvant to modulate acquired anti-malaria immunity induced by malaria-specific antigen(s). As disclosed herein, α-GalCer administration to mice immunized with sub-optimal doses of (i) irradiated Plasmodium yoelii sporozoites, (ii) synthetic peptides corresponding to either the CD8+ T cell epitope or the CD4+ T cell epitopes of the CS protein or (iii) recombinant viruses expressing the whole CS protein or the CD8+ T cell epitope of the CS protein greatly enhances protective anti-malaria immunity. In addition, α-GalCer-treatment was found herein to elicit a higher level of protection even four weeks after sporozoite immunization, indicating that a longer lasting protective immunity could be elicited by the conjoint administration of α-GalCer.

The main immune components affected by the α-GalCer administration appear to be malaria-specific CD8+ and CD4+ T cells that secrete IFN-γ. In the present study, the levels of the humoral response as well as the Th2-type response were unaltered by the α-GalCer treatment. In contrast, the administration of α-GalCer increased the number of IFN-γ-secreting CS-specific CD4+ and CD8+ T cells induced by γ-spz immunization approximately 5-fold and 7-fold, respectively. Furthermore, the level of the CS-specific T cell responses remained much higher at six weeks after γ-spz immunization in α-GalCer-treated mice compared to that in non-treated mice. Since protective immunity against the liver stages of malaria is primarily mediated by CD8+ T cells as well as CD4+ T cells, and requires production of IFN-γ (Schofield et al., Nature 330: 664-666, 1987; Weiss et al., Proc. Natl. Acad. Sci. USA, 85: 573-576,1988; Doolan and Hoffman. J. Immunol., 165: 1453-1462, 2000), it is not surprising that the level of anti-malaria protection is increased and its duration prolonged by the α-GalCer treatment.

The adjuvant effect of α-GalCer was also observed when the α-GalCer-treated mice were immunized with synthetic peptides corresponding to the CD4+ and CD8+ epitopes or with recombinant viruses expressing either the *P. yoelii* CS protein or the H-2Kd-restricted CD8+ T cell epitope of this protein. These results confirm and extend the data obtained by γ-spz immunization, indicating that malaria-specific CD8+ and CD4+ T cell responses are enhanced by α-GalCer administration, regardless of the type of immunogen used (whole parasite, or peptide, or recombinant virus). It is also demonstrated herein that the CD8+ T cell response enhanced by α-GalCer administration is independent of the CD8+ T cell epitope used, since the immune response induced by a recombinant Sindbis virus expressing a H-2Dd-restricted T cell epitope of HIV was also enhanced.

α-GalCer's ability to augment the level of protective anti-malaria immunity induced by γ-spz immunization requires both CD1d molecules and Vα14 NKT cells. Without these components, α-GalCer was unable to increase the protection elicited by a sub-optimal dose of the immunogen. Although both CD1d molecules and Vα14 NKT cells were needed for α-GalCer's ability to augment protective anti-malaria immunity, a noticeable increase in the number of CS-specific CD8+ T cells was detected in Jα281-deficient mice after α-GalCer-treatment. This may be due to the high degree of genetic heterogeneity of these mice, which affects the T cell response and causes this moderate increase. Alternatively, CD1d-reactive, non-Vα14 NKT cells may exist in Jα281-deficient mice.

While the precise molecular mechanism of the adjuvant effect of α-GalCer remains to be fully clarified, the present finding that these activities of α-GalCer are eliminated in mice lacking IFN-γ receptor indicates that IFN-γ is important in mediating the adjuvant effect of α-GalCer. It is possible that IFN-γ secreted by NKT and/or NK cells acts on antigen presenting cells, by up-regulating the MHC class I processing machinery, e.g., TAP, proteasome subunits and class I heavy chains. Alternatively, IFN-γ may enhance the acquired cell-mediated immune response by directly acting on antigen-specific CD8+ T cells.

The instant kinetic studies demonstrate that α-GalCer displays a maximal adjuvant effect only when the glycolipid is co-administered with an antigen (such as irradiated plasmodial sporozoites [γ-spz], or malaria-specific peptide epitopes [e.g., presented by recombinant viruses]) and that the administration of α-GalCer two days prior to or two days after the immunization with these immunogens led to lack of adjuvant activity. A recent study on the in vivo kinetics of NKT cells after α-GalCer administration using CD1d/α-GalCer tetramers, has indicated that murine NKT cells, especially those in the liver where they constitute 20-30% of the lymphocyte population, are promptly activated, secrete large amounts of IFN-γ and IL-4, and readily disappear 5 hours after the stimulation (Matsuda et al., J. Exp. Med., 192: 741-754, 2000). Interestingly, this acute disappearance of α-GalCer-activated NKT cells was also confirmed by phenotypic analysis of the peripheral blood of cancer patients treated with α-GalCer.

As previously shown by various investigators, NKT cell activation not only causes activation of NK cells but also proliferation of memory CD4+ and CD8+ T cells (Eberl et al., J. Immunol., 165: 4305-4311, 2000) or induction of the early activation marker CD69 on the surface of T cells and B cells (Nishimura et al., Int. Immunol. 12: 987-994, 2000), suggesting a role for activated NKT cells in initiating T cell and B cell responses. Also, recent studies by a number of different investigators indicate that IFN-γ is secreted by both NKT and NK cells after α-GalCer treatment (Nishimura et al., Int. Immunol. 12: 987-994, 2000; Camaud et al., J. Immunol., 163: 4647-4650, 1999; Eberl and MacDonald, Eur. J. Immunol., 30: 985-992, 2000). In one of these studies it has been shown that administration of α-GalCer to mice immunized with a T cell lymphoma enhances the generation of tumor-specific cytotoxic T cells (Nishimura et al., Int. Immunol. 12: 987-994,2000). However, as to whether α-GalCer-activated NKT cells can contribute to the induction of protective immunity against pathogens or tumors has not been elucidated. In this regard, the present study indicates for the first time that α-GalCer-activated NKT cells play a role in the induction of protective immunity, in which specific CD8+ T cells are the primary effector cells.

In conclusion, this study has shown that α-GalCer acts as an adjuvant to enhance and/or extend the duration of protective antigen-specific immune responses. Specifically, as disclosed herein, this α-GalCer-mediated immunostimulation is at least in part attributed to the α-GalCer-activated NKT cells. Although an endogenous mammalian counterpart of α-GalCer has yet to be identified, it is conceivable that it would be also induced under a range of pathological and inflammatory conditions to activate NKT cells (Mieza et al., J. Immunol., 156:4035-4040, 1996; Sumida et al., J. Exp. Med., 182:1163-1168, 1995). Accordingly, the studies disclosed herein may present evidence for a role of NKT cells in bridging innate and adaptive immunity.

The present findings on the adjuvant activity of α-GalCer are clearly applicable not only to malaria, but also to various other intracellular microbial pathogens, as well as to other infections and tumors. Finally, since it has been demonstrated that α-GalCer can stimulate not only murine but also human NKT cells (Brossay et al., J. Exp. Med. 188: 1521-1528, 1998; Spada et al., J. Exp. Med., 188: 1529-1534, 1998), instant findings can be directly applied to the understanding of the role of human NKT cells, and the design of novel, more effective human vaccines.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

All patents, applications, publications, test methods, literature, and other materials cited herein are hereby incorporated by reference.

What is claimed is:

1. A method for augmenting the immune response induced by an antigen in a mammal comprising conjointly administering to said mammal (i) a recombinant vector expressing an antigen selected from the group consisting of a protein, peptide, and glycoprotein, wherein said recombinant vector that expresses said antigen is selected from a recombinant adenovirus, a recombinant Sindbis virus, naked DNA, and naked RNA, and (ii) a pharmaceutical composition comprising an immunogenically effective amount of an adjuvant comprising a glycosylceramide of the general Formula 1:

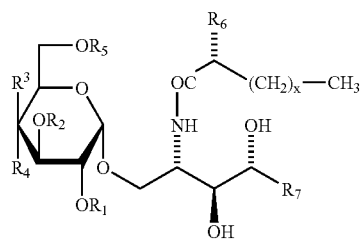

wherein $R_1$, $R_2$ and $R_5$ represent H or a monosaccharide; $R_3$ and $R_6$ represent H or OH, respectively; $R_4$ represents H, OH or a monosaccharide; X denotes an integer from 1 to 23; $R_7$ represents any one of the following groups (a)-(g): (a) $-(CH_2)_{11}-CH_3$, (b) $-(CH_2)_{12}-CH_3$, (c) $-(CH_2)_{13}-CH_3$, (d) $-(CH_2)_9-CH(CH_3)_2$, (e) $-(CH_2)_{10}-CH(CH_3)_2$, (f) $-(CH_2)_{11}-CH(CH_3)_2$, and (g) $-(CH_2)_{11}-CH(CH_3)-C_2H_5$.

2. A method for augmenting the immune response induced by a malaria antigen to a susceptible mammalian host comprising conjointly administering to said host (i) a recombinant vector expressing at least one isolated malaria-specific sporozoite surface antigen selected from the group consisting of a protein, peptide, and glycoprotein, wherein said recombinant vector that expresses said antigen is selected from a recombinant adenovirus, a recombinant Sindbis virus, naked DNA, and naked RNA in a first amount, and (ii) α-galactosylceramide (α-GalCer) as an immune adjuvant in a second amount;

said first and second amounts being effective in combination to enhance or prolong the immune response mounted against said antigen by the host compared to the immune response that the host could have mounted upon the administration of said first amount of said recombinant vector without the conjoint administration of said adjuvant.

3. The method of claim 2, wherein said α-GalCer is (2S, 3S,4R)-1—O-(α-D-galactopyranosyl)-2-(N-hexacosanoylamino)-1,3,4-octadecanetriol.

4. The method of claim 2, wherein said recombinant vector and said adjuvant are administered simultaneously.

5. The method of claim 2, wherein said malaria-specific antigen comprises a T cell epitope of the plasmodial circumsporozoite (CS) protein.

6. The method of claim 5, wherein said T cell epitope has an amino acid sequence selected from the group consisting of YNRNIVNRLLGDALNGKPEEK (SEQ ID NO: 1), SYVPSAEQI (SEQ ID NO: 2), $(NVDPNANP)_n$ (SEQ ID NO: 3), and EYLNKIQNSLSTEWSPC SVT (SEQ ID NO: 4).

7. The method of claim 2, wherein said enhancement or prolonging of the duration of the immune response is manifested by the enhancement or extension of the duration of antigen-specific CD8+ T cell responses.

8. The method of claim 2, wherein said first amount is in the range of 0.1 μg-100 mg per kg of body weight.

9. The method of claim 2, wherein said second amount is in the range of 10-100 μg per kg of body weight.

10. The method of claim 1, wherein said glycosylceramide is selected from the group consisting of α-galactosylceramide (α-GalCer), α-glucosylceramide (α-GlcCer), Galα1-6Galα1-1'Cer, Galα1-6Glcα1-1'Cer, Galα1-2Galα1-1'Cer, and Galβ1-3Galα1-1'Cer.

11. The method of claim 10, wherein said α-GalCer is (2S,3S,4R)-1—O-(α-D-galactopyranosyl)-2-(N-hexacosanoylamino)-1,3,4-octadecanetriol.

12. The method of claim 1, wherein said recombinant vector and said adjuvant are administered simultaneously.

13. The method of claim 1, wherein said antigen is malaria-specific.

14. The method of claim 13, wherein said malaria-specific antigen comprises a T cell epitope of the malarial circumsporozoite (CS) protein.

15. The method of claim 1, wherein said mammal is human.

16. The method of claim 1, wherein said recombinant vector is selected from (1) a recombinant adenovirus expressing the *P. yoelii* CS protein, AdPyCS, (2) a recombinant Sindbis virus expressing the CD8+ T cell epitope (SYVPSAEQI [SEQ ID NO: 2]) of *P. yoelii* CS protein, SIN(Mal), (3) a recombinant Sinbis virus expressing the CD8+ T cell epitope (RGPGRAFVTI [SEQ ID NO: 5]) of HIV p18 protein, SIN(P18), and (4) a recombinant Sindbis virus expressing a CD8+ T cell epitope TYQRTRALV (SEQ ID NO: 16) of the nucleoprotein (NP) of the influenza A virus.

17. The method of claim 2, wherein said recombinant vector is a recombinant adenovirus expressing the *P. yoelii* CS protein, AdPyCS, or a recombinant Sindbis virus expressing the CD8+ T cell epitope (SYVPSAEQI [SEQ ID NO: 2]) of *P. yoelii* CS protein, SIN(Mal).

* * * * *